(12) United States Patent
Fujiwara et al.

(10) Patent No.: US 9,046,488 B2
(45) Date of Patent: Jun. 2, 2015

(54) NONLINEAR OPTICAL DEVICE, MULTIPHOTON MICROSCOPE, AND ENDOSCOPE

(75) Inventors: Masato Fujiwara, Hachioji (JP); Kenji Taira, Kodaira (JP)

(73) Assignee: OLYMPUS CORPORATION, Tokyo (JP)

( * ) Notice: Subject to any disclaimer, the term of this patent is extended or adjusted under 35 U.S.C. 154(b) by 325 days.

(21) Appl. No.: 13/419,661

(22) Filed: Mar. 14, 2012

(65) Prior Publication Data

US 2012/0238820 A1  Sep. 20, 2012

(30) Foreign Application Priority Data

Mar. 16, 2011 (JP) ................................ 2011-058053
Sep. 22, 2011 (JP) ................................ 2011-207030

(51) Int. Cl.
| | |
|---|---|
| H01S 3/10 | (2006.01) |
| G01N 21/64 | (2006.01) |
| A61B 5/00 | (2006.01) |
| G01N 21/63 | (2006.01) |
| G02B 21/06 | (2006.01) |
| G02B 23/24 | (2006.01) |
| G02B 21/00 | (2006.01) |
| H01S 3/00 | (2006.01) |

(52) U.S. Cl.
CPC .......... *G01N 21/6458* (2013.01); *A61B 5/0075* (2013.01); *G01N 21/636* (2013.01); *G01N 2201/0697* (2013.01); *G02B 21/06* (2013.01); *G02B 23/2469* (2013.01); *H01S 3/0057* (2013.01); *G02B 21/0008* (2013.01)

(58) Field of Classification Search
CPC .................. G02B 21/0008; G01N 2201/0697; H01S 3/0057
USPC ........................................ 359/337.5; 372/25
See application file for complete search history.

(56) References Cited

U.S. PATENT DOCUMENTS 6,178,041 B1 * 1/2001 Simon ........................... 359/368
2008/0260319 A1 * 10/2008 Taira et al. ....................... 385/1

OTHER PUBLICATIONS

Williams, J.A.R., et al., "Fiber Bragg Grating Fabrication for Dispersion Slope Compensation", IEEE Photon. Technol. Letters, vol. 8, No. 9, pp. 1187-1189, (1996).

* cited by examiner

*Primary Examiner* — Eric Bolda
(74) *Attorney, Agent, or Firm* — Scully, Scott, Murphy & Presser, P.C.

(57) ABSTRACT

Provided is a nonlinear optical device capable of alleviating, without the need for a complicated compensation mechanism, temporal broadening and the waveform distortion resulting from a group-velocity dispersion slope, to thereby irradiate an object with short optical pulses having high peak power. The nonlinear optical device includes a short optical pulse source (10) for generating short optical pulses and a short optical pulse delivery system (20) for delivering the short optical pulses generated from the short optical pulse source to an object, in which there is generated substantially no nonlinear optical effect and there is substantially no amount of group-velocity dispersion, the short optical pulse source generates short optical pulses, and the short optical pulses have a spectral width (full width at half maximum) $\lambda_{FWHM}$ satisfying $\lambda_1 < \lambda_{FWHM} < \lambda_2$.

26 Claims, 21 Drawing Sheets

NONLINEAR OPTICAL DEVICE, MULTIPHOTON MICROSCOPE, AND ENDOSCOPE

CROSS-REFERENCE TO RELATED APPLICATION

The present application claims priority from Japanese Application No. 2011-207030, filed on Sep. 22, 2011, and from Japanese Application No. 2011-058053, filed on Mar. 16, 2011, the contents of which are incorporated herein by reference.

TECHNICAL FIELD

The present invention relates to a nonlinear optical device for irradiating an object with short optical pulses so as to induce second-order nonlinear optical effects, and also relates to a multiphoton microscope and endoscope using the nonlinear optical device.

RELATED ART

In recent years, sub-picosecond ultrashort optical pulses, having high peak power and a plurality of wavelength components, have been used in various fields, such as biology, medicine, medical care, processing, and measurement. In particular, in the fields of biology and medicine, an optical pulse source that generates ultrashort optical pulses, such as a titanium: sapphire laser and a fiber laser, has been frequently used in a microscope using nonlinear optical effects, such as a multiphoton fluorescence microscope and a harmonic generation microscope; a gene transfer apparatus using optical stress waves; a diffuse optical tomography apparatus; and the like.

In these fields, ultrashort optical pulses are used for the purpose of inducing nonlinear optical effects in an object to be irradiated with the ultrashort optical pulses. When the ultrashort optical pulses irradiated onto the object are higher in peak power, nonlinear optical effects are induced with higher efficiency.

Meanwhile, a short optical pulse delivery system such as a lens or an optical fiber is generally used for delivering ultrashort optical pulses generated in an optical pulse source to an object. However, ultrashort optical pulses having high peak power are known to be temporally broadened and suffer waveform distortion in the process of propagating through the short optical pulse delivery system, due to the group-velocity dispersion (GVD) effects in the short optical pulse delivery system and the nonlinear optical effects such as a self-phase modulation (SPM) effects induced in the short optical pulse delivery system. Such temporal broadening of optical pulses and waveform distortion of optical pulses lead to problems in many applications.

For example, in a nonlinear optical microscope such as a multiphoton fluorescence microscope, which requires ultrashort optical pulses having high peak power, if the pulses are temporally broadened or the pulses suffer waveform distortion in a short optical pulse delivery system such as an optical fiber, the short optical pulses are reduced in peak power accordingly, leading to a reduction in efficiency in multiphoton excitation, which results in a problem that the microscope image is reduced in brightness.

Therefore, it is critically important to suppress to a minimum the temporal broadening and waveform distortion of optical pulses in the short optical pulse delivery system.

In view of the above, it is widely practiced to alleviate or compensate these GVD effects and nonlinear optical effects in the short optical pulse delivery system. For example, for the purpose of alleviating the GVD effects, a short optical pulse delivery system that is low in GVD may be used, or a dispersion generator for compensating the GVD may be included in the short optical pulse delivery system. Meanwhile, the nonlinear optical effects are particularly noticeable when the short optical pulse delivery system includes a lengthy optical fiber, which requires specific measures to be taken. Except for such a case, however, the nonlinear optical effects hardly result in a problem.

On the other hand, as to a group-velocity dispersion slope, which is high-order GVD, there has been proposed a mechanism for compensating the group-velocity dispersion slope (see, for example, "J. A. R. Williams, L. A. Everall, I. Bennion, 'Fiber Bragg grating fabrication for dispersion slope compensation,' IEEE Photon. Technol. Lett., 8, pp. 1187-1189 (1996)"). This mechanism can be provided in a short optical pulse delivery system or the like, so as to compensate waveform distortion of the short optical pulses due to the influence of group-velocity dispersion slope.

DISCLOSURE OF THE INVENTION

Means for Solving the Problem

A non-linear optical device according to the first aspect of the invention for irradiating an object with short optical pulses so as to generate second-order nonlinear optical effects, includes:

a short optical pulse source for generating short optical pulses; and a short optical pulse delivery system for delivering, to the object, the short optical pulses generated from the short optical pulse source, in which there is generated substantially no nonlinear optical effect in the nonlinear optical device, there is substantially no amount of group-velocity dispersion in the nonlinear optical device, and the short optical pulses generated by the short optical pulse source have a spectral width (full width at half maximum) $\lambda_{FWHM}$ satisfying:

$$\lambda_1 < \lambda_{FWHM} < \lambda_2 \quad (1),$$

under the following conditions:

$$\lambda_1 = \frac{a\lambda_c^2}{cT_2} \quad (2)$$

$$\lambda_2 = \frac{a\lambda_c^2}{cT_1} \quad (3)$$

$$T_1 = 2\sqrt{-p}\cos\left(\frac{u}{3} + \frac{4\pi}{3}\right) + \frac{(kD_{3d})^{1/3}}{\alpha \cdot 2^{2/3}} \quad (4)$$

$$T_2 = 2\sqrt{-p}\cos\left(\frac{u}{3}\right) + \frac{(kD_{3d})^{1/3}}{\alpha \cdot 2^{2/3}} \quad (5)$$

$$p = -\left(\frac{-1}{\alpha 2^{2/3}(kD_{3d})^{1/3}}\right)^2 \quad (6)$$

$$u = \cos^{-1}\left(\frac{q}{p\sqrt{-p}}\right) \quad (7)$$

$$q = -\left(\frac{-1}{\alpha 2^{2/3}(kD_{3rd})^{-1/3}}\right)^3 + \frac{kD_{3rd}}{2} \quad (8)$$

where
a, k: parameters determined depending on the pulse waveform,
$\lambda_c$: the central wavelength of the pulses,
c: the speed of light,
$D_{3d}$: the total amount of group-velocity dispersion slope, and
$\alpha=0.5$.

According to the second aspect of the invention, in the nonlinear optical device according to the first aspect, the following conditions are satisfied:

$$\sum_{\substack{propagation \\ medium}} \gamma \cdot P_{peak} \cdot L \leq 1 \quad (9)$$

$$\frac{D_{2d}}{T_0^2} \leq 1 \quad (10)$$

$$\frac{D_{3d}}{T_0^3} \geq 1, \quad (11)$$

where $\gamma$ represents the nonlinear coefficient of each propagation medium in the short optical system, $P_{peak}$ represents a higher one of the peak power values of the short optical pulses before and after being delivered through each propagation medium, L represents the physical length of each propagation medium in the short optical pulse delivery system, $D_{2d}$ represents the total amount of group-velocity dispersion in the nonlinear optical device, $D_{3d}$ represents the total amount of group-velocity dispersion slope in the nonlinear optical device, and $T_0$ represents the temporal width of the short optical pulses obtained when the output intensity of the short optical pulses becomes 1/e of the peak power in the temporal width at the Fourier transform limit calculated from the spectral width of the short optical pulses.

Here, description is given of Fourier transform-limited short optical pulses. Fourier transform-limited pulses are substantially unchirped short optical pulses, in which the product of the temporal width and the frequency width of short optical pulses expressed by Expression (12) becomes minimum. The minimum value varies depending on the waveform of short optical pulses, which is given as 0.441 when the pulses have a Gaussian waveform and as 0.315 when the pulses have a hyperbolic secant (sech) waveform.

$$T_{FWHM} f_{FWHM} \quad (12)$$

According to the third aspect of the invention, in the nonlinear optical device according to the first aspect, the parameter k satisfies 0.35<k<0.55.

The parameter k varies depending on the pulse waveform, and given as 0.535 when the pulses have a Gaussian waveform while as 0.370 when the pulses a hyperbolic secant (sech) waveform. In general, it is rare that short optical pulses emitted from a short optical pulse source have a perfect one of the Gaussian waveform and the hyperbolic secant waveform. The parameter k is defined to fall within the range of 0.35<k<0.55 so that it can be associated with a waveform intermediate between those two pulse waveforms.

According to the forth aspect of the invention, in the nonlinear optical device according to the first aspect, the short optical pulse source includes: a short optical pulse generation device for generating substantially unchirped short optical pulses; and a chirp adding device for adding chirp to the short optical pulses generated from the short optical pulse generation device.

According to the fifth aspect of the invention, in the nonlinear optical device according to the first aspect, the short optical pulse source includes a spectral width adjusting mechanism.

With this configuration, an optimal spectral width calculated from the total group-velocity dispersion slope in the nonlinear optical device can be defined, so that nonlinear optical effects can be efficiently generated in an object irradiated with short optical pulses.

According to the sixth aspect of the invention, in the nonlinear optical device according to the first aspect, the short optical pulse source generates short optical pulses having a spectral width of 0.5 nm or more.

When the short optical pulses have a spectral width of 0.5 nm or more, the object can be irradiated with short optical pulses having high peak power, so that high second-order nonlinear optical effects are expected to be generated in the object.

According to the seventh aspect of the invention, in the nonlinear optical device according to the first aspect, the short optical pulse delivery system includes a dispersion generator.

With this configuration, the group-velocity dispersion generated in the nonlinear optical device such as a short optical pulse delivery system can be compensated, so as to irradiate short optical pulses having high peak power onto an object to be irradiated with short optical pulses, so that the nonlinear optical effects are efficiently generated.

According to the eighth aspect of the invention, in the nonlinear optical device according to the first aspect, the short optical pulse delivery system includes a hollow core photonic crystal fiber.

According to the ninth aspect of the invention, in the nonlinear optical device including the hollow core photonic crystal fiber according to the eighth aspect, the short optical pulse source emits short optical pulses having a wavelength at which the hollow core photonic crystal fiber has group-velocity dispersion reduced to zero.

This configuration eliminates the need to provide a dispersion generator for compensating the group-velocity dispersion of the short optical pulse delivery system, thereby making the device configuration simpler.

According to the tenth aspect of the invention, in the nonlinear optical device according to the eighth aspect, the short optical pulse source emits short optical pulses having a wavelength at which the nonlinear optical device has total group-velocity dispersion reduced to zero.

With this configuration, the total sum of the group-velocity dispersion of the hollow core photonic crystal fiber and of the other optical systems (such as an objective lens) is reduced to zero, making the device configuration simpler while irradiating short optical pulses having high peak power onto an object to be irradiated with short optical pulses, to thereby efficiently generate nonlinear optical effects.

A multiphoton microscope according to the eleventh aspect of the invention includes the nonlinear optical device according to the first aspect, and detects the second-order nonlinear effects generated from the object.

An endoscope according to the twelfth aspect of the invention includes the nonlinear optical device according the first aspect, and detects the second-order nonlinear effects generated from the object.

A nonlinear optical device according to the thirteenth aspect of the invention for irradiating an object with short optical pulses so as to generate second-order nonlinear optical effects includes:

a short optical pulse source for generating short optical pulses; and a short optical pulse delivery system for delivering the short optical pulses generated from the short optical pulse source to the object, in which there is generated substantially no nonlinear optical effect in the nonlinear optical device, there is substantially no amount of group-velocity dispersion in the nonlinear optical device, and the short optical pulses generated by the short optical pulse source have a pulse temporal width (full width at half maximum) $T_{FWHM}$ satisfying the following range:

$$T_1 < T_{FWHM} < T_2 \qquad (13)$$

under the following conditions:

$$T_1 = 2\sqrt{-p}\cos\left(\frac{u}{3} + \frac{4\pi}{3}\right) + \frac{(kD_{3d})^{1/3}}{\alpha \cdot 2^{2/3}} \qquad (14)$$

$$T_2 = 2\sqrt{-p}\cos\left(\frac{u}{3}\right) + \frac{(kD_{3d})^{1/3}}{\alpha \cdot 2^{2/3}} \qquad (15)$$

$$p = -\left(\frac{-1}{\alpha 2^{2/3}(kD_{3d})^{-1/3}}\right)^2 \qquad (16)$$

$$u = \cos^{-1}\left(\frac{q}{p\sqrt{-p}}\right) \qquad (17)$$

$$q = -\left(\frac{-1}{\alpha 2^{2/3}(kD_{3rd})^{-1/3}}\right)^3 + \frac{kD_{3rd}}{2} \qquad (18)$$

where
k: parameter determined depending on the pulse waveform,
$D_{3d}$: the total amount of group-velocity dispersion slope, and
$\alpha=0.5$ According to the fourteenth aspect of the invention, in the nonlinear optical device according to the thirteenth aspect, the following conditions are satisfied:

$$\sum_{\substack{propagation \\ medium}} \gamma \cdot P_{peak} \cdot L \leq 1 \qquad (19)$$

$$\frac{D_{2d}}{T_0^2} \leq 1 \qquad (20)$$

$$\frac{D_{3d}}{T_0^3} \geq 1 \qquad (21)$$

where $\gamma$ represents the nonlinear coefficient of each propagation medium in the short optical system, $P_{peak}$ represents a higher one of the peak power values of the short optical pulses before and after being delivered through each propagation medium, L represents the physical length of each propagation medium in the short optical pulse delivery system, $D_{2d}$ represents the total amount of group-velocity dispersion, $D_{3d}$ represents the total amount of group-velocity dispersion slope, and $T_0$ represents the temporal width of the short optical pulses obtained when the output intensity of the short optical pulses becomes 1/e of the peak power.

According to the fifteenth aspect of the invention, in the nonlinear optical device according to the thirteenth aspect, the short optical pulse source generates short optical pulses satisfying the following expression:

$$T_{FWHM} \cdot f_{FWHM} \leq 0.88 \qquad (22)$$

where $f_{FWHM}$ represents the spectral half width (full width at half maximum) of the short optical pulses generated by the short optical pulse source.

According to the sixteenth aspect of the invention, in the nonlinear optical device according to the thirteenth aspect, the parameter k satisfies $0.35 < k < 0.55$.

According to the seventeenth aspect of the invention, in the nonlinear optical device according to the thirteenth aspect, the short optical pulse source includes: a short optical pulse generation device for generating chirped short optical pulses; and a chirp compensation device for compensating chirp of the short optical pulses generated from the short optical pulse generation device.

According to the eighteenth aspect of the invention, in the nonlinear optical device according to the seventeenth aspect, the chirp compensation device includes a diffraction grating.

According to the nineteenth aspect of the invention, in the nonlinear optical device according to the seventeenth aspect, the chirp compensation device includes a prism.

According to the twentieth aspect of the invention, in the nonlinear optical device according to the thirteenth aspect, the short optical pulse delivery system includes a group-velocity dispersion compensation device.

According to the twenty first aspect of the invention, in the nonlinear optical device according to the twentieth aspect, the group-velocity dispersion compensation device includes a diffraction grating.

According to the twenty second aspect of the invention, in the nonlinear optical device according to the twentieth aspect, the group-velocity dispersion compensation device includes a prism.

According to the twenty third aspect of the invention, in the nonlinear optical device according to the thirteenth aspect, the short optical pulse delivery system includes a hollow core photonic crystal fiber.

According to the 24th aspect of the invention, in the nonlinear optical device according to the thirteenth aspect, the short optical pulse source generates short optical pulses having a temporal width of 1 picosecond or less.

When the short optical pulses have a temporal width of 1 picosecond or less, the short optical pulses with high peak power can be generated, and high second-order nonlinear optical effects are expected to be generated in an object.

A multiphoton microscope according to the 25th aspect of the invention includes the nonlinear optical device according to the thirteenth aspect, in which second-order nonlinear effects generated by the object are detected.

An endoscope according to the 26th aspect of the invention includes the nonlinear optical device according the thirteenth aspect, in which second-order nonlinear effects generated by the object are detected.

BEST MODES FOR CARRYING OUT THE INVENTION

Prior to the description of embodiments of the present invention, a basic configuration of the present invention and the rationale therefor are explained.

Figure 1:
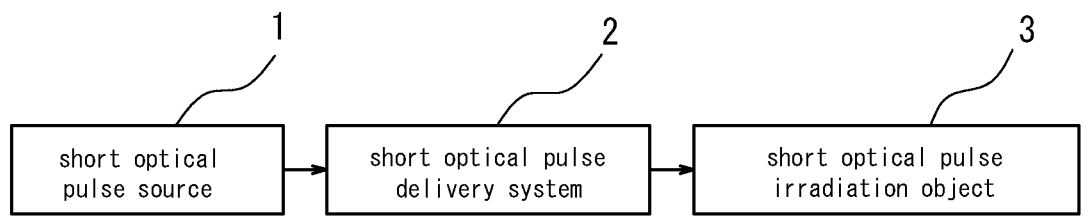
FIG. 1 is a block diagram illustrating a basic configuration of a nonlinear optical device according to the present invention.

FIG. 1 is a diagram illustrating a basic configuration of a nonlinear optical device according to the present invention. The nonlinear optical device includes a short optical pulse source 1 for generating short optical pulses and a short optical pulse delivery system 2 for delivering the short optical pulses generated from the short optical pulse source 1 to an object to be irradiated with short optical pulses (hereinafter, referred to as object) 3. Here, the nonlinear optical device irradiates the object 3 with short optical pulses, to thereby generate second-order nonlinear optical effects such as two-photon fluorescence and second harmonic generation. Signal light such as two-photon fluorescence and second harmonic generated from the object 3 is detected by, for example, a detector (not shown).

The optical system including the short optical pulse source 1 and the short optical pulse delivery system 2 may be configured so as to be capable of suppressing or compensating the nonlinear optical effects and the total group-velocity dispersion by a known method. On the other hand, it is not easy to compensate the total amount of group-velocity dispersion slope, and hence the total amount of group-velocity dispersion slope remains non-negligible. In such a case, the waveform deformation or distortion generated in short optical pulses results mainly from the group-velocity dispersion slope.

The nonlinear optical effects and the total amount of group-velocity dispersion in the nonlinear optical device are preferred to satisfy the above-mentioned conditional expressions (9) and (10). When Expression (9) is satisfied, the nonlinear optical effects in the nonlinear optical device are small enough to be negligible. When Expression (10) is satisfied, the amount of group-velocity dispersion in the nonlinear optical device is small enough to be negligible. When Expression (9) and Expression (10) are satisfied and further Expression (11) is satisfied, the group-velocity dispersion slope in the nonlinear optical device is non-negligible. When these conditional expressions are satisfied, the nonlinear optical effects and the group-velocity dispersion generated in the short optical pulse optical system are reduced to be small enough to be negligible. As a result, a waveform change resulting from the group-velocity dispersion slope noticeably occurs.

Figure 2:
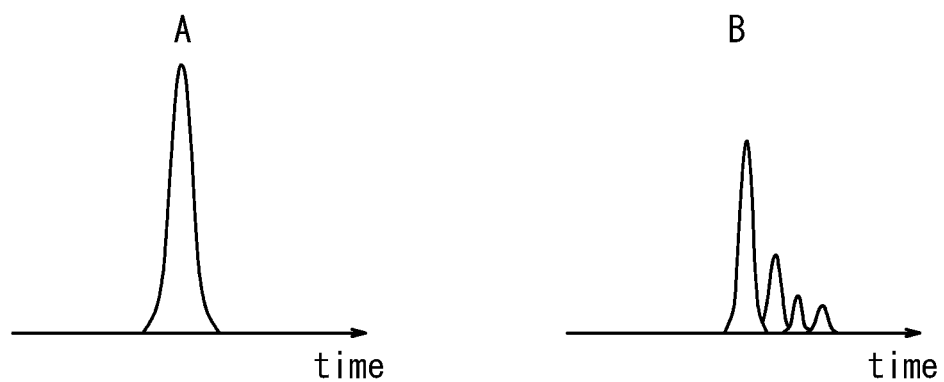
FIG. 2 are diagrams illustrating a waveform distortion resulting from a group-velocity dispersion slope in the nonlinear optical device.

FIGS. 2A and 2B are diagrams illustrating a waveform change in short optical pulses resulting from the group-velocity dispersion slope in the nonlinear optical device. FIG. 2A shows a temporal waveform of short optical pulses immediately after being emitted from the short optical pulse source 1, and FIG. 2B shows a temporal waveform of short optical pulses having exited from the short optical pulse delivery system 2. It shows that the short optical pulses have ringing generated in the temporal waveform thereof and suffer waveform distortion, after being delivered through the short optical pulse delivery system. Such a waveform distortion leads to a reduction in peak power of the short optical pulses, with the result that the nonlinear optical effects to be generated in an object irradiated with the short optical pulses are reduced in efficiency.

Under the above-mentioned conditions, first, with no consideration given to the total amount of group-velocity dispersion slope in the short optical pulse delivery system, the signal light amount $F_{noD}$ [W] per unit time to be generated by the second-order nonlinear optical effects in the object irradiated with short optical pulses is expressed as Expression (23) below. (reference: Winfried Denk, James H. Strickler, Watt W. Webb, "Two-Photon Laser Scanning Fluorescence Microscopy", Science, 248, pp. 73-76, 1990)

$$F_{noD} = \frac{A \cdot P_{ave}^2}{f_{rep} \cdot T_{FWHM}} = \frac{A \cdot P_{ave}^2}{f_{rep}} \cdot \frac{c\lambda_{FWHM}}{a\lambda_c^2} \tag{23}$$

In Expression (23), A is a coefficient of an order of [1/W], $P_{ave}$ represents an average power per unit time of the short optical pulses, $f_{rep}$ represents a repetition frequency of the short optical pulses, c represents the speed of light, $\lambda_{FWHM}$ represents a spectral width (full width at half maximum) of the short optical pulses, and a represents a parameter obtained by multiplying a temporal width by a frequency (spectral) width of the short optical pulses, the temporal width and the frequency (spectral) width both defining the Fourier-transform limit of the short optical pulses. The parameter a varies depending on the waveform of the short optical pulses, which is given as 0.441 when the pulses have a Gaussian waveform and as 0.315 when the pulses have a hyperbolic secant (sech) waveform.

The expression (15) shows that the signal light amount $F_{noD}$ generated in an object to be irradiated with short optical pulses is higher as the spectral width $\lambda_{FWHM}$ of the short optical pulses is wider.

However, it is generally known that the waveform distortion in the short optical pulses resulting from the group-velocity dispersion slope becomes larger as the spectral width grows wider.

This is also obvious from Expression (11). The expression (11) shows the ratio of the total amount of group-velocity dispersion slope to the spectral wave form. When the ratio increases in value, the waveform distortion in the short optical pulses resulting from the group-velocity dispersion slope becomes larger.

Then, Expression (11) is expressed as follows with the spectral width $\lambda_{FWHM}$, and it can be understood that the value of Expression (11) increases as the spectral width becomes larger.

$$\frac{D_{3d}}{T_0^3} = \frac{D_{3d}}{(T_{FWHM}/b)^3} = b^3 D_{3d} \left(\frac{c\lambda_{FWHM}}{a\lambda_c^2}\right)^3 \propto \lambda_{FWHM}^3 \qquad (24)$$

In Expression (24), b is a parameter correlating $T_0$ to $T_{FWHM}$, and defined as in Expression (25). The parameter b is given as 1.665 when the pulses have a Gaussian waveform, while given as 1.763 when the pulses have a hyperbolic secant (sech) waveform.

$$T_{FWHM} = b T_0 \qquad (25)$$

Accordingly, the above argument testifies that there is an optimal spectral width of short optical pulses for most efficiently generating the second-order nonlinear optical effects in an object to be irradiated with short optical pulses when a group-velocity dispersion slope exists in the nonlinear optical device.

However, there has been found no document indicating the presence of such an optimal spectral width and disclosing any specific method of deriving the optimal spectral width. According to the present invention, the optimal spectral width is derived as a function of the group-velocity dispersion slope.

In the following, description is given of how to derive the efficiency of the second-order nonlinear optical effects in an object to be irradiated with short optical pulses when a group-velocity dispersion slope exists in the nonlinear optical device.

With consideration given to the total amount of group-velocity dispersion slope in the short optical pulse delivery system, the signal light amount $F_{noD}$ is obtained by multiplying Expression (23) by Expression (26), under the influence of the waveform distortion in the short optical pulses.

$$\frac{(a\lambda_c^2/c\lambda_{FWHM})^3}{(a\lambda_c^2/c\lambda_{FWHM})^3 + k \cdot D_{3d}}, \qquad (26)$$

where k is a parameter determined by the waveform of the short optical pulses, and $D_{3d}$ represents the total amount of group-velocity dispersion slope.

Further, the parameter k is obtained as a result of experiments made by changing the total group-velocity dispersion slope, and the waveform and spectral width of the short optical pulses. The parameter k is given as 0.535 when the pulses have a Gaussian waveform, and as 0.370 when the pulses have a hyperbolic secant (sech) waveform. The parameter k takes an intermediate value between those two values when the pulses have a waveform intermediate between the Gaussian and the sech.

Then, the signal light amount F to be generated by the second-order nonlinear optical effects in the object to be irradiated with the short optical pulses is expressed as Expression (27) below, which is obtained by multiplying Expression (23) by Expression (26).

$$F = \frac{A \cdot P_{ave}^2}{f_{rep}} \cdot \frac{(a\lambda_c^2/c\lambda_{FWHM})^2}{(a\lambda_c^2/c\lambda_{FWHM})^3 + k \cdot D_{3d}} \qquad (27)$$

Figure 3:
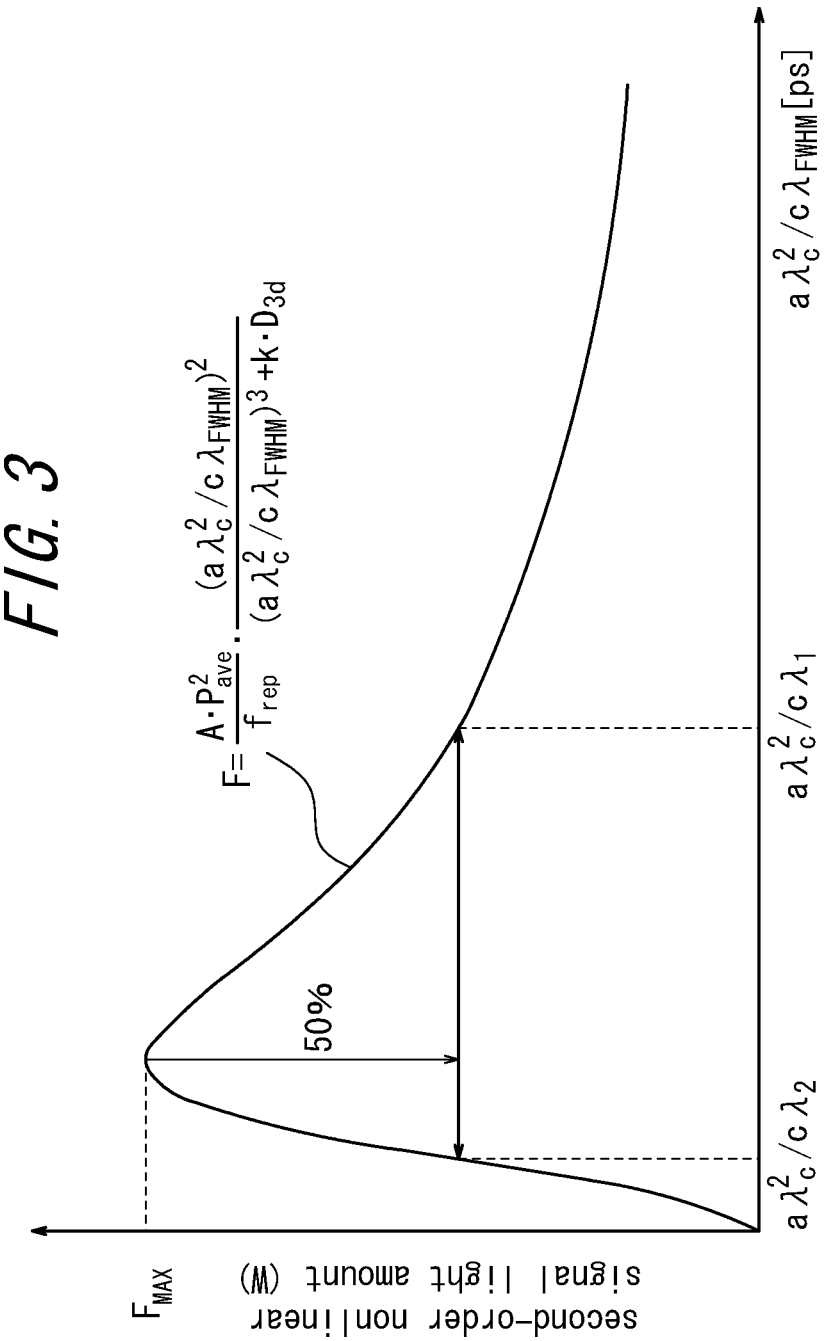
FIG. 3 is a graph showing a relation between the signal light amount generated by the second-order nonlinear optical effects and a spectral width of short optical pulses emitted from a short optical pulse source.

FIG. 3 shows Expression (27) in a graph which has, on abscissa, a parameter $(a\lambda_c^2/c\lambda_{FWHM})$ associated with the spectral width of the short optical pulses.

As shown in FIG. 3, in the case where the total amount of group-velocity dispersion slope in the short optical pulse delivery system is too large to be negligible, the signal light amount F generated by the second-order nonlinear optical effects in an object irradiated with short optical pulses becomes substantially maximum ($F_{MAX}$) when the short optical pulses have a spectral width falling within a range of $\lambda_1 < \lambda_{FWHM} < \lambda_2$. The signal light amount F resulting from the second-order nonlinear optical effects significantly decreases when the short optical pulses have a spectral width that greatly falls out of the range.

Here, in view of the fluorescence intensity in two-photon fluorescence observation and thermal damage to an object irradiated with short optical pulses, it is preferred to use short optical pulses having $\lambda_{FWHM}$ that falls within the spectral range $(\lambda_1 < \lambda_{FWHM} < \lambda_2)$ in which the signal light amount F generated by the second-order nonlinear optical effects decreases from its highest value ($F_{MAX}$) to 50% ($\alpha=0.5$) thereof. Further, in view of the sensitivity of the detector, it is preferred to use short optical pulses having $\lambda_{FWHM}$ that falls within a range in which the signal light amount F to be generated is 60% or more of its highest value ($F_{MAX}$), and more preferably 70% or more depending on the observation object. For detecting weak signals, it is further preferred that $\lambda_{FWHM}$ fall within a range in which the signal light amount F to be generated is 80% or more of its highest value.

The parameters $\lambda_1$, $\lambda_2$ defining the optimal spectral width $\lambda_{FWHM}$ described above of short optical pulses are obtained from Expressions (2) to (8) below.

$$\lambda_1 = \frac{a\lambda_c^2}{cT_2} \qquad (2)$$

$$\lambda_2 = \frac{a\lambda_c^2}{cT_1} \qquad (3)$$

-continued $$T_1 = 2\sqrt{-p}\cos\left(\frac{u}{3} + \frac{4\pi}{3}\right) + \frac{(kD_{3rd})^{1/3}}{\alpha \cdot 2^{2/3}} \quad (4)$$

$$T_2 = 2\sqrt{-p}\cos\left(\frac{u}{3}\right) + \frac{(kD_{3rd})^{1/3}}{\alpha \cdot 2^{2/3}} \quad (5)$$

$$p = -\left(\frac{-1}{\alpha 2^{2/3}(kD_{3d})^{-1/3}}\right)^2 \quad (6)$$

$$u = \cos^{-1}\left(\frac{q}{p\sqrt{-p}}\right) \quad (7)$$

$$q = -\left(\frac{-1}{\alpha 2^{2/3}(kD_{3rd})^{-1/3}}\right)^3 + \frac{kD_{3rd}}{2} \quad (8)$$

where
a, k: parameters determined depending on the pulse waveform,
$\lambda_c$: the central wavelength of the pulses,
c: the speed of light,
$D_{3d}$: the total amount of group-velocity dispersion slope, and
$\alpha$=0.5.

As described above, a is a parameter obtained by multiplying a temporal width with a frequency (spectral) width of the short optical pulses, the temporal width and the frequency (spectral) width both defining the Fourier-transform limit of the short optical pulses. The parameter a varies depending on the waveform of the short optical pulses, and is given as 0.441 when the pulses have a Gaussian waveform, while given as 0.315 when the pulses have a hyperbolic secant (sech) waveform.

As described above, k is a parameter obtained as a result of experiments, and varies depending on the waveform of the short optical pulses. The parameter k is given as 0.535 when the pulses have a Gaussian waveform and as 0.370 when the pulses have a hyperbolic secant (sech) waveform. The parameters a and k each take an intermediate value between the above-mentioned two values when the pulses have a waveform intermediate between the Gaussian and the sech.

Therefore, in the nonlinear optical device according to the present invention, the spectral width $\lambda_{FWHM}$ is defined so as to satisfy the above-mentioned requirements, so that the influences of temporal broadening and waveform distortion of optical pulses resulting from the group-velocity dispersion slope can be alleviated without the need for a mechanism for compensating the group-velocity dispersion slope, to thereby irradiate an object with short optical pulses having high peak power.

In the following, embodiments of the present invention are described with reference to the accompanying drawings.

First Embodiment

Figure 4:
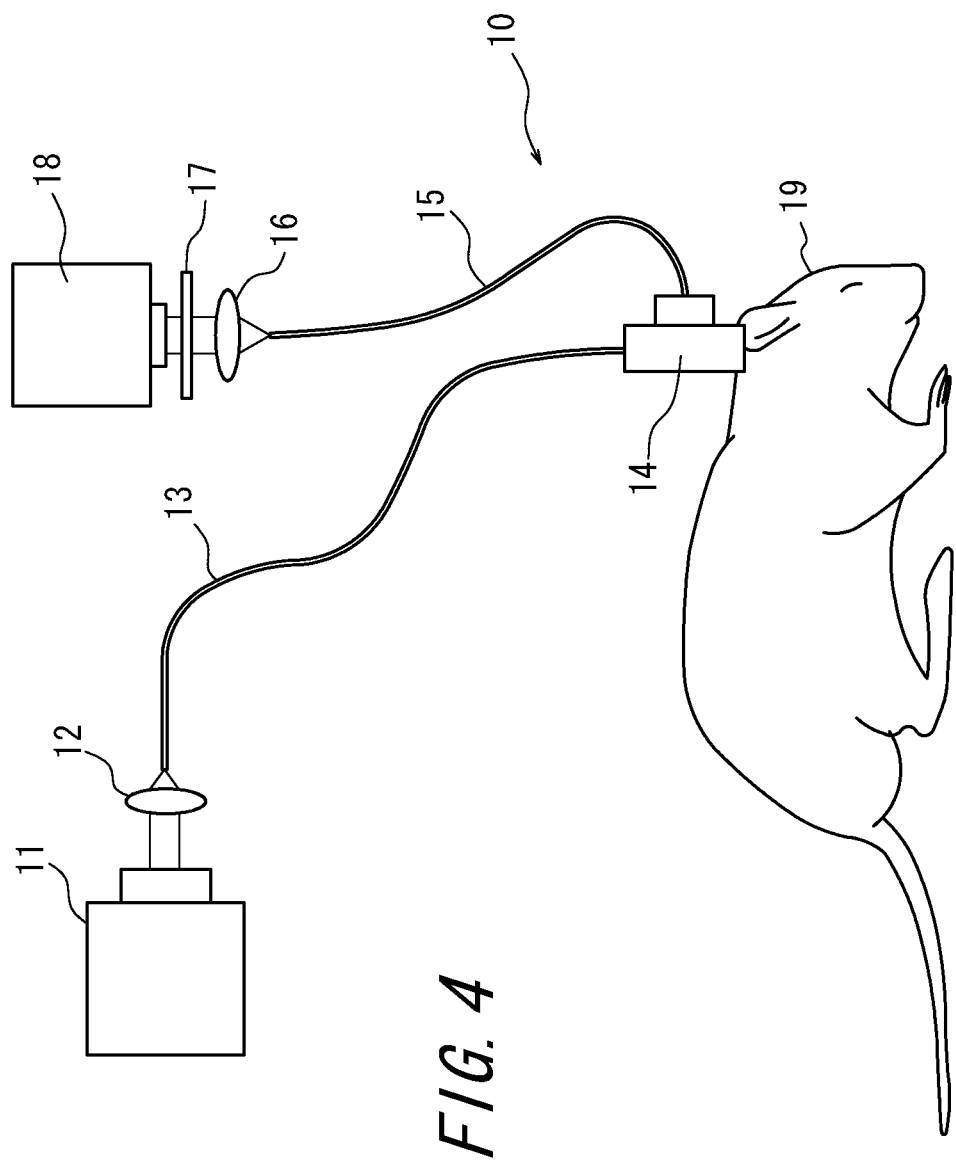
FIG. 4 is a schematic configuration diagram of a compact microscope nonlinear optical device according to a first embodiment of the present invention.

FIG. 4 is a schematic configuration diagram of a compact microscope nonlinear optical device 10 according to a first embodiment of the present invention. This embodiment includes a microscope downsized as a micro head 14, which is fixed to the head of a small laboratory animal such as a mouse, so as to observe an organ such as a mouse brain without anesthesia.

The compact microscope nonlinear optical device includes: a short optical pulse source 11 for generating chirped Gaussian short optical pulses; a lens 12; a hollow core photonic crystal fiber 13; the micro head 14; a multi-mode optical fiber 15; a lens 16; a barrier filter 17; and a detector 18.

The short optical pulse source 11 is for emitting chirped short optical pulses, and configured, for example, as a light source using a titanium: sapphire laser for generating Gaussian short optical pulses having a wavelength of 800 nm in the near-infrared region. The short optical pulse source 11 emits chirped short optical pulses, with an average power of 2 W, a repetition frequency of 80 MHz, a temporal width (full width at half maximum) of 300 fs, and a spectral width (full width at half maximum) of 7.8 nm.

The hollow core photonic crystal fiber 13 has group-velocity dispersion reduced to zero at a light wavelength of 800 nm. However, the group-velocity dispersion still remains in an optical system such as the lens 12. In view of this, the device is configured to add chirp in advance to optical pulses in the short optical pulse source 11 so that substantially unchirped pulses are irradiated onto an observation object 19 such as a mouse to be irradiated with short optical pulses.

As illustrated in FIG. 4, short optical pulses emitted from the short optical pulse source 11 are incident on the hollow core photonic crystal fiber 13 by means of the lens 12, and delivered, through the hollow core photonic crystal fiber 13, to the micro head 14 which is attached and fixed to the observation object 19 such as the head of a mouse.

Figure 5:
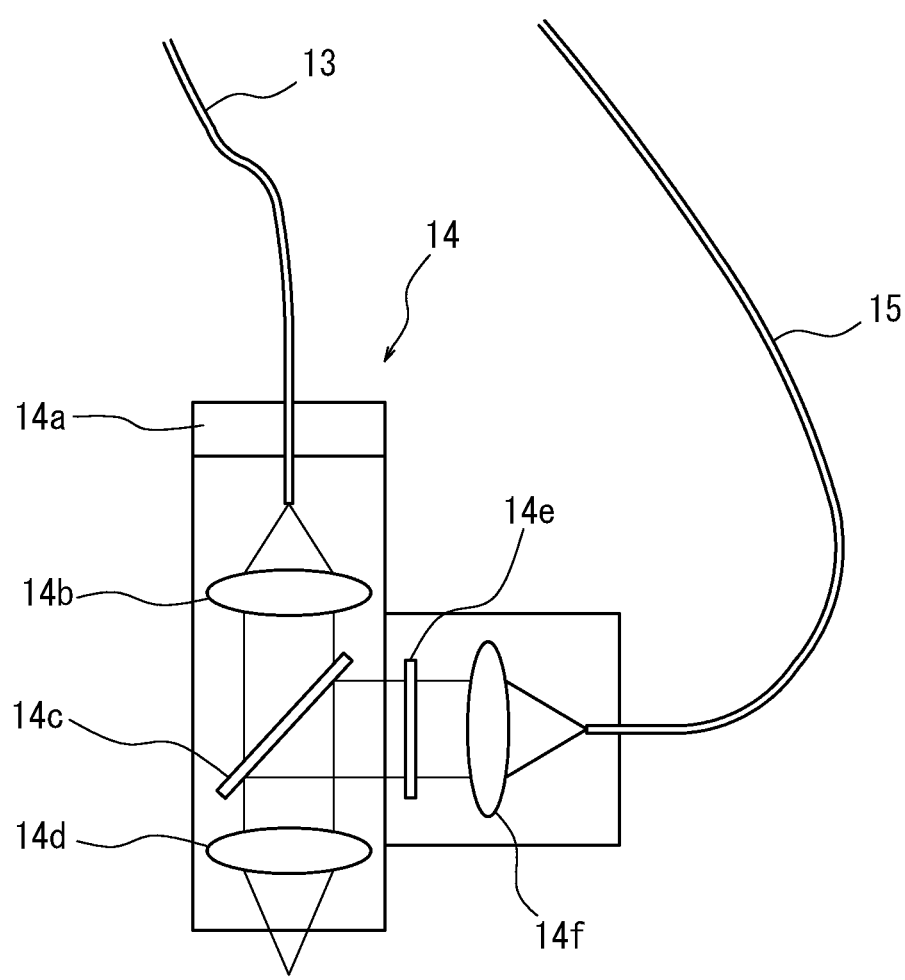
FIG. 5 is a diagram illustrating a detailed configuration of a micro head of FIG. 4.

FIG. 5 is a diagram illustrating a detailed configuration of the micro head 14 of FIG. 4. The micro head 14 includes: a piezo XY scanner 14a; a lens 14b; a spectral mirror 14c; an objective lens 14d; a barrier filter 14e; and a lens 14f. The piezo XY scanner 14a is coupled to the leading end of the hollow core photonic crystal fiber 13 introduced into the micro head 14. Further, the spectral mirror 14c has spectral characteristics of transmitting short optical pulses while reflecting signal light generated from the observation object irradiated with short optical pulses. Short optical pulses having exited from the hollow core photonic crystal fiber 13 are collimated by the lens 14b, and pass through the spectral mirror 14c so as to be irradiated via the objective lens 14a onto a desired position on a mouse as the observation object 19. At this time, the piezo XY scanner 14a is driven, to thereby sequentially scan pulse irradiation positions on the observation object 19.

For example, when the observation object 19 is a mouse brain, two-photon fluorescence and second harmonic generated through the irradiation of short optical pulses pass through the objective lens 14d so as to be reflected by the spectral mirror 14c, then pass through the barrier filter 14e for cutting off stray light resulting from the short optical pulses, and are focused by the lens 14f so as to be incident on the multi-mode fiber 15.

After that, as illustrated in FIG. 4, the signal light is delivered through multi-mode fiber 15 which is large in diameter, so as to pass through the lens 16 and the barrier filter 17, and is detected by the detector 18. The detector 18 is connected to an image processing device (not shown), together with the piezo XY scanner 14a, so that a two-dimensional microscope image can be formed based on the signal light intensity obtained by the detector 18 and the information on the short optical pulse irradiation position on the observation object 19.

Figure 6:
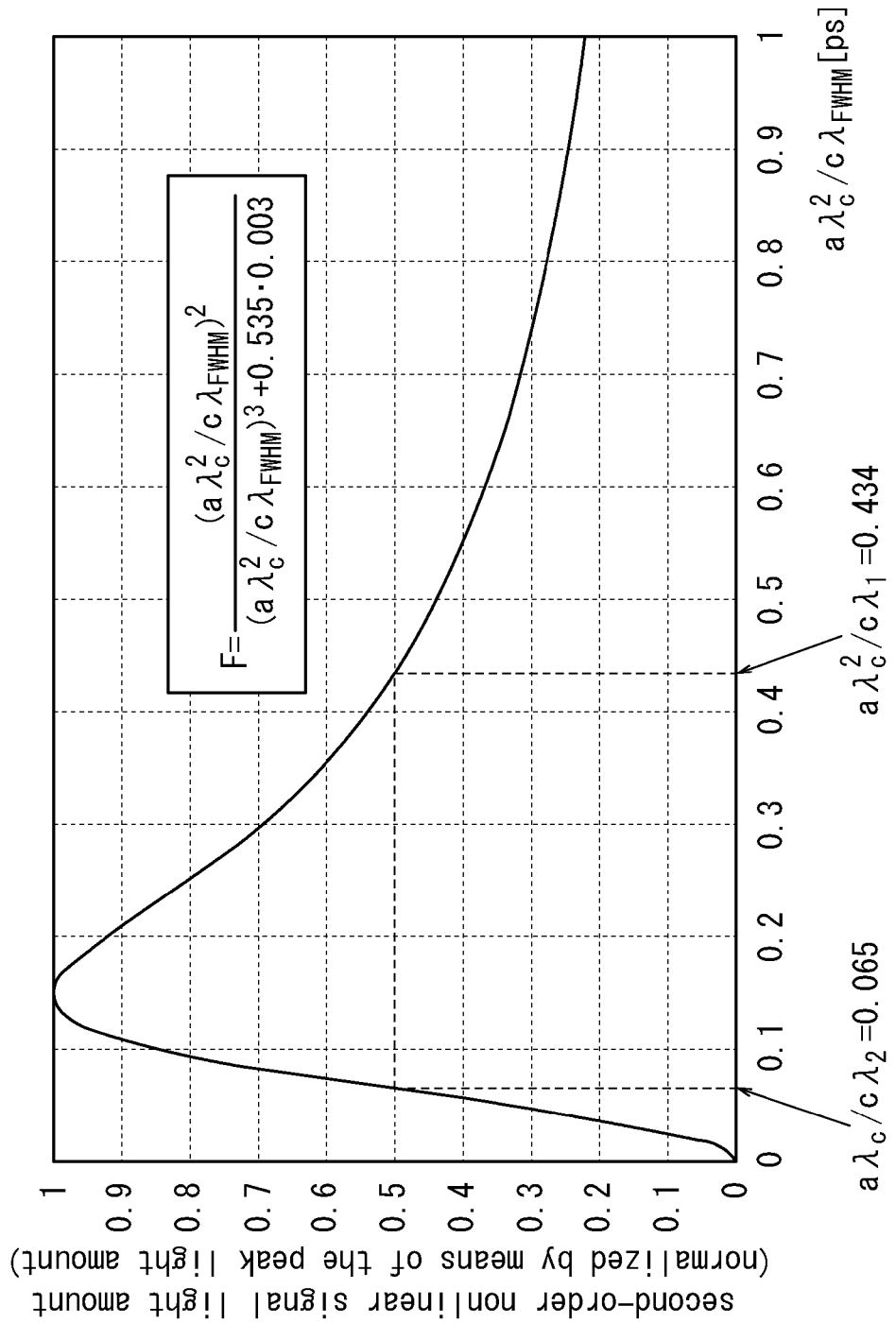
FIG. 6 is a graph showing a relation between the signal light amount generated by the second-order nonlinear optical effects and a spectral width of optical pulses emitted from a short optical pulse source according to the first embodiment.

FIG. 6 is a graph showing a relation between the signal light amount F generated by the second-order nonlinear optical effects and a spectral width $a\lambda_c^2/c\lambda_{FWHM}$ of optical pulses emitted from the short optical pulse source according to the first embodiment. Then, it is preferred to irradiate short optical pulses satisfying the following range:

$$0.065 < a\lambda_c^2/c\lambda_{FWHM} < 0.434$$

in order to efficiently generate second-order nonlinear optical effects in the mouse as the observation object 19. Based on the range thus defined, the range of an optimal spectral width (full width at half maximum) of short optical pulses was obtained as follows:

$$\lambda_1 = 2.2 \text{ nm} \qquad (5)$$

$$\lambda_2 = 14.5 \text{ nm}.$$

Accordingly, for efficient generation of the second-order nonlinear optical effects in an observation object to be irradiated with short optical pulses, there may be used short optical pulses having a spectral width satisfying the following range:

$$2.2 \text{ nm} < \lambda_{FWHM} < 14.5 \text{ nm}. \qquad (15)$$

The short optical pulses generated from the short optical pulse source 11 have a spectral width (full width at half maximum) of 7.8 nm, which falls within the above-mentioned range.

Short optical pulses immediately after being emitted from the short optical pulse source 11 have $T_{FWHM}$ and $f_{FWHM}$ which are calculated as follows:

$$T_{FWHM} \times f_{FWHM} = 1.2.$$

As a result, the hollow core photonic crystal fiber 13 has zero group-velocity dispersion at a light wavelength of 800 nm, while the group-velocity dispersion still remains in an optical system such as the lens 12. In view of this, the optical device is configured to add chirp in advance to optical pulses in the short optical pulse source 11 so that substantially unchirped pulses are irradiated onto the observation object 19 such as a mouse to be irradiated with short optical pulses, which eliminates the need to additionally provide a dispersion compensator such as a diffraction grating pair.

In this embodiment, the short optical pulse source 11 is configured to emit chirped short optical pulses. However, similar effects can be obtained even when the short optical pulse source 11 generates pulses as Fourier-transform limited pulses that have substantially no chirp, as long as the short optical pulse delivery system is configured to irradiate substantially unchirped pulses onto the observation object 19.

In deriving the above-mentioned preferred range of $\lambda_{FWHM}$, assuming that the short optical pulse source 11 generates Gaussian short optical pulses, parameters are defined as follows:
a=0.441;
k=0.535;
$D_{3d}$=0.003 ps$^3$; and
α=0.5,
which were assigned in Expressions (2) to (8), to thereby obtain $\lambda_{FWHM}$.

Here, how to derive k and $D_{3d}$ is briefly described. First, k is a parameter depending on the waveform of short optical pulses, and can be factorized into two factors as $k=k_1 \times k_2$.

When short optical pulses suffer waveform distortion resulting from the group-velocity dispersion slope, such waveform distortion leads to a decrease in the signal light amount F to be generated from the object irradiated with the short optical pulses. The parameter $k_1$ represents a coefficient relevant to the decrease.

To be more specific, the signal light amount $F_{noD}$ generated by the second order nonlinear optical effects in the object to be irradiated with short optical pulses can be expressed by Expression (23) as described above, when there is no group-velocity dispersion slope or when the group-velocity dispersion slope is small enough to be negligible.

$$F_{noD} = \frac{A \cdot P_{ave}^2}{f_{rep}} \cdot \frac{c\lambda_{FWHM}}{a\lambda_c^2} \qquad (23)$$

However, when the amount of group-velocity dispersion slope in the system is not negligible, $F_{noD}$ is obtained by multiplying Expression (23) by Expression (26).

$$\frac{(a\lambda_c^2/c\lambda_{FWHM})^3}{(a\lambda_c^2/c\lambda_{FWHM})^3 + k \cdot D_{3d}} \qquad (26)$$

The expression (26) is rewritable as follows.

$$\frac{(a\lambda_c^2/c\lambda_{FWHM})^3}{(a\lambda_c^2/c\lambda_{FWHM})^3 + k \cdot D_{3d}} = \frac{1}{1 + \frac{k \cdot D_{3d}}{(a\lambda_c^2/c\lambda_{FWHM})^3}} \qquad (28)$$

$$= \frac{1}{1 + \frac{k_1 \cdot k_2 \cdot D_{3d}}{(a\lambda_c^2/c\lambda_{FWHM})^3}}$$

$$= \frac{1}{1 + \frac{k_1 \cdot k_2 \cdot D_{3d}}{T_{FWHM}^3}}$$

$$= \frac{1}{1 + \frac{k_1 \cdot D_{3d}}{T_0^3}}$$

The signal light amount F generated by the second-order nonlinear optical effects is obtained by multiplying Expression (23) by Expression (28). Accordingly, Expression (28) demonstrates that the signal light amount F decreases along with the increase of $k_1$, when light sources different in pulse temporal width ($T_0$) at the Fourier transform limit are provided and pulses are made incident on an optical system having a group-velocity dispersion slope of $D_{3d}$, so as to estimate the signal light amount to be generated by the second-order nonlinear optical effects. Here, $k_1$ represents a coefficient at this time, which is obtained based on the experimental results. This value is obtained as $k_1$=0.116 with Gaussian short optical pulses.

Further, $k_2$ is the cube of a ratio between the full width at half maximum $T_{FWHM}$ of the short optical pulse waveform and the width $T_0$ at which the signal intensity becomes 1/e, which are expressed as follows accordingly:

$$T_{FWHM} = \sqrt[3]{k_2} \cdot T_0 \qquad (29),$$

and $k_2$ is obtained as $1.665^3$ with Gaussian pulses.

Therefore, k is calculated by multiplying $k_1$ by $k_2$, and obtained as 0.535.

Next, how to derive the value of the group-velocity dispersion slope $D_{3d}$ is described. To derive $D_{3d}$, only $D_{3d1}$ generated from the hollow core photonic crystal fiber 13 may be taken into consideration. The reason is that the group-velocity dispersion slope generated from other components such as the lens 32 is extremely small enough to be negligible, as compared to the group-velocity dispersion slope generated from the hollow core photonic crystal fiber 13. Similarly, third or higher-order phase change in the spectrum of the short optical pulse source 11 can also be negligible.

Therefore, $D_{3d1}$ to be generated in the hollow core photonic crystal fiber 33 that is 3 m in length is obtained as follows at the wavelength of 800 nm:

$$D_{3d}=0.003 \text{ ps}^3.$$

Accordingly, the total group-velocity dispersion slope $D_{3d}$ is obtained as:

$$D_{3d}=0.003 \text{ ps}^3.$$

As described above, according to this embodiment, there is provided a nonlinear optical device that includes a Gaussian short optical pulse source and a short optical pulse delivery system, in which substantially no nonlinear optical effect is generated in the nonlinear optical device and substantially no group-velocity dispersion is generated in the nonlinear optical device while the spectral width $\lambda_{FWHM}$ (full width at half maximum) of short optical pulses generated by the short optical pulse source satisfies the range of 2.2 nm<$\lambda_{FWHM}$<14.5 nm defined by Expression (1) which is obtained based on Expressions (2) to (8). Accordingly, the temporal broadening and waveform distortion of optical pulses resulting from a group-velocity dispersion slope are alleviated so that it is possible to irradiate an object with short optical pulses having high peak power.

Further, when the conditions defined by Expressions (19), (20), (21) are satisfied, the nonlinear optical effects and the group-velocity dispersion effects in the nonlinear optical device are small enough to be negligible, and hence a waveform change resulting from the group-velocity dispersion slope prominently appears in short optical pulses. Thus, the use of ultrashort optical pulses with the above-mentioned temporal width is particularly effective.

Further, the hollow core photonic crystal fiber 13 is provided and the short optical pulse source 11 is adapted to emit light having a wavelength that reduces to zero the group-velocity dispersion in the hollow core photonic crystal fiber 13, which eliminates the need to provide a dispersion generator for compensating the group-velocity dispersion in the short optical pulse delivery system, making the device configuration simple.

Further, the short optical pulse source 11 emits short optical pulses having a wavelength that reduces to zero the total group-velocity dispersion in the nonlinear optical device, so that the total sum of the group-velocity dispersions of the hollow core photonic crystal fiber 13 and of other optical systems (such as an objective lens) is reduced to zero, which makes the device configuration simple while making it possible to irradiate short optical pulses having high peak power onto an object to be irradiated with short optical pulses, to thereby efficiently generate nonlinear optical effects.

Further, the short optical pulse source 11 generates short optical pulses that have a spectral width of 0.5 nm or more, and hence short optical pulses to be irradiated onto an object have high peak power. Accordingly, high-order nonlinear optical effects, namely, second-order nonlinear optical effects are expected to be generated in the object.

Second Embodiment

Figure 7:
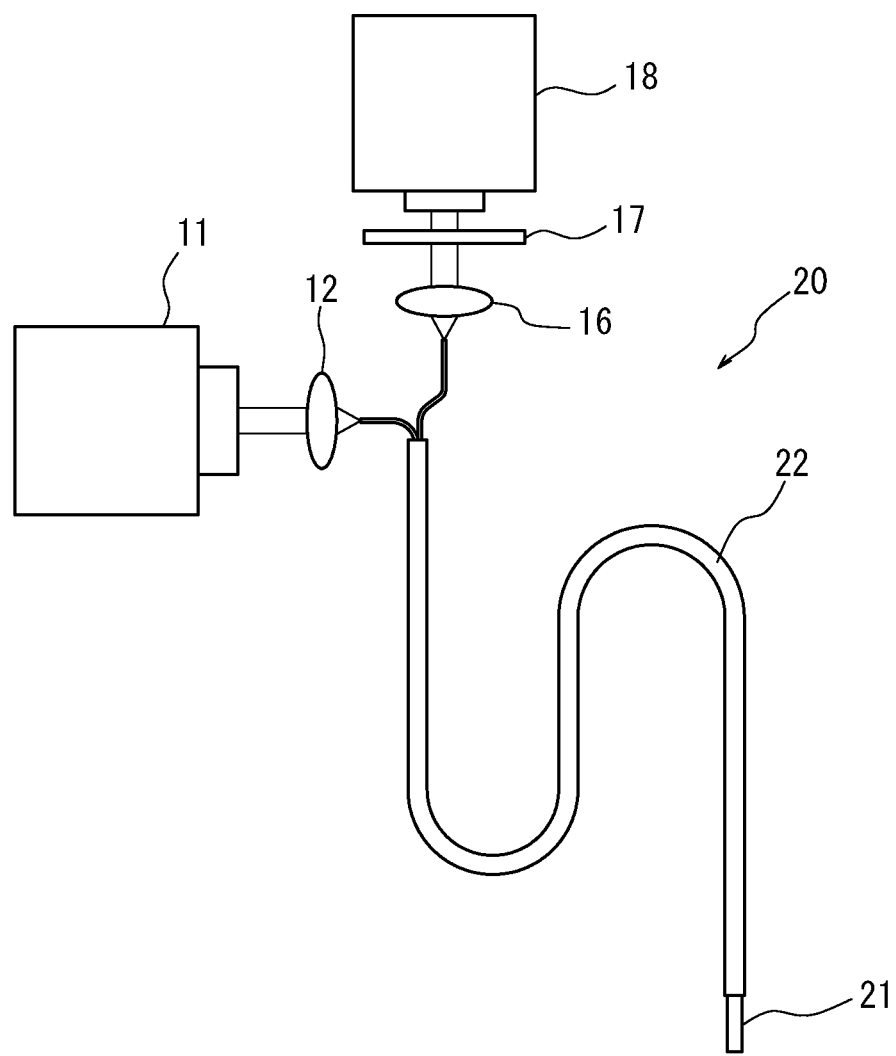
FIG. 7 is a schematic configuration diagram of an endoscope nonlinear optical device according to a second embodiment of the present invention.

FIG. 7 is a schematic configuration diagram of an endoscope nonlinear optical device 20 according to a second embodiment of the present invention. This embodiment is different from the first embodiment of FIG. 4 in that the micro head 14 is formed as a hard part 21 and the hollow core photonic crystal fiber 13 and the multi-mode fiber 15 connected to the hard part 21 are bundled together into one so as to be configured as a flexible insertion part 22. The flexible insertion part 22 may be used alone or may be inserted into a clamp hole of a conventional endoscope, to thereby use the device as an endoscope nonlinear optical device 20. With this configuration, the device can be configured as an endoscope nonlinear optical device and still can produce the similar effects as in the first embodiment.

Third Embodiment

Figure 8:
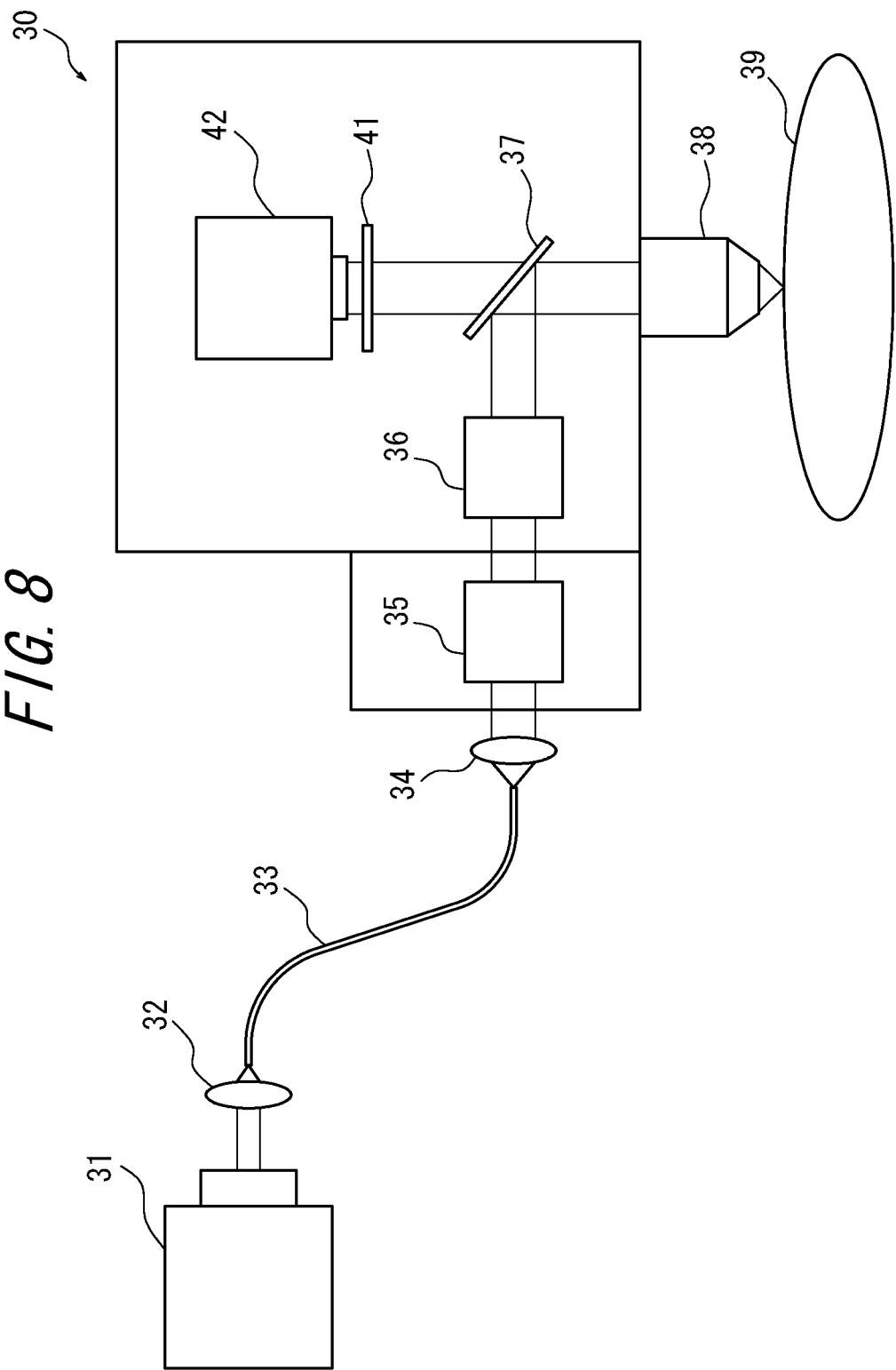
FIG. 8 is a schematic configuration diagram of a microscope nonlinear optical device according to a third embodiment of the present invention.

FIG. 8 is a schematic configuration diagram of a microscope nonlinear optical device 30 according to a third embodiment of the present invention. The microscope nonlinear optical device 30 is configured by including: a short optical pulse source 31 for generating sech short optical pulses; a lens 32; a hollow core photonic crystal fiber 33; a lens 34; a dispersion generator 35; a Galvano mirror 36; a spectral mirror 37; an objective lens 38; a barrier filter 41; and a detector 42.

The short optical pulse source 31 is configured, for example, as a light source using a titanium: sapphire laser for generating sech short optical pulses having a wavelength of 1030 nm in the near-infrared region. The short optical pulse source 31 emits chirped short optical pulses, with an average power of 0.5 W, a repetition frequency of 80 MHz, a temporal width (full width at half maximum) of 370 fs, and a spectral width (full width at half maximum) of 11 nm.

The lens 32, the hollow core photonic crystal fiber 33, the lens 34, the dispersion generator 35, the Galvano mirror 36, the spectral mirror 37, and the objective lens 38 form a short optical pulse delivery system which delivers short optical pulses emitted from the short optical pulse source 31 to the observation object 39 to be observed. Here, the spectral mirror 37 is a dichroic mirror that has frequency characteristics of passing signal light generated from the observation object 39 irradiated with short optical pulses while reflecting short optical pulses delivered from the short optical pulse source 31.

The dispersion generator 35 is a device for compensating a second-order phase change in the spectrum of the short optical pulse source 31 and the total group-velocity dispersion in the optical system from the lens 32 to the observation object 39.

Figure 9:
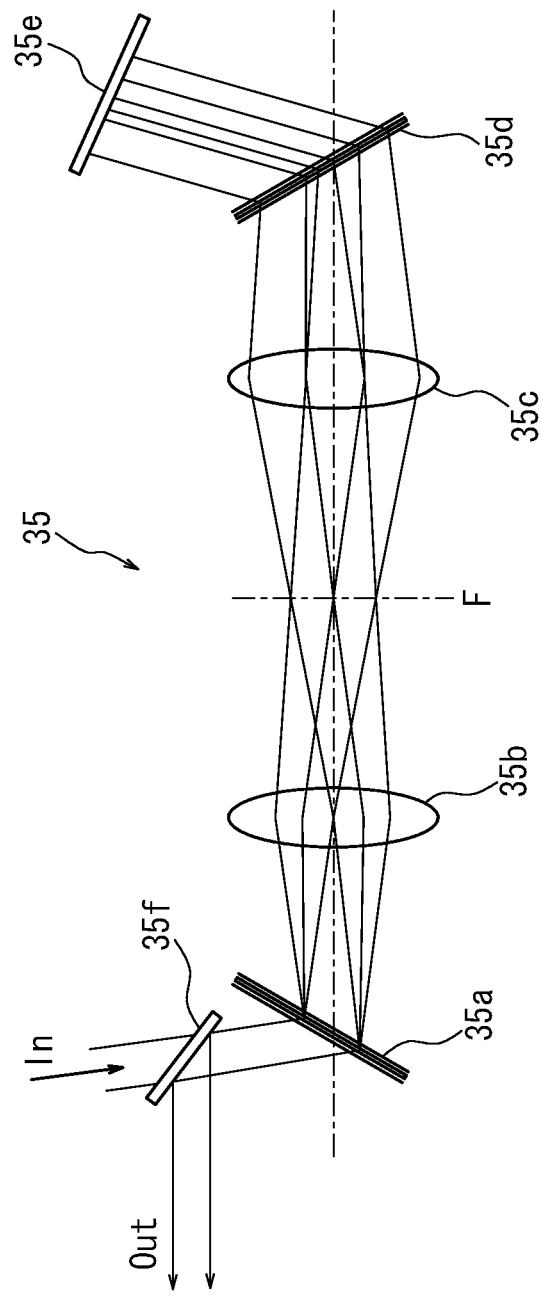
FIG. 9 is a configuration diagram illustrating an example of a dispersion generator of FIG. 8.

FIG. 9 is a diagram illustrating a detailed configuration of the known dispersion generator 35 using diffraction gratings. The dispersion generator 35 is configured by including: diffraction gratings 35a, 35d; lenses 35b, 35c; and mirrors 35e, 35f. Chirped short optical pulses emitted from the short optical pulse source 31 are incident on the diffraction grating 35a and diffracted so as to be subjected to angular dispersion due to the wavelength component. Further, the short optical pulses thus broadened by the angular dispersion pass through the lenses 35b, 35c to be diffracted again by the diffraction grating 35d, so as to be converted into parallel light and reflected by the mirror 35e. The light thus reflected passes through the diffraction grating 35d, the lenses 35c, 35b, and the diffraction grating 35a, so as to be reflected by the mirror 35f, and exits therefrom. As a result, group-velocity dispersion is generated, which compensates a second-order phase change in the spectrum of the short optical pulse source 31 and the total group-velocity dispersion in the optical system from the lens 32 to the observation object 39.

The dispersion generator 35 is not limited to the one that includes diffraction gratings, and may be any device that generates wavelength dispersion using a prism, a glass block, a chirp mirror, or the like.

Next, description is given of an operation of the microscope nonlinear optical device 30 in its entirety. Light emitted from the short optical pulse source 31 passes through the lens 32 to be incident on the hollow core photonic crystal fiber 33. The short optical pulses having exited from the hollow core photonic crystal fiber 33 are collimated by the lens 34, and incident on the dispersion generator 35 so as to be subjected to dispersion.

The short optical pulses having exited from the dispersion generator 35 are sequentially reflected by the Galvano mirror 36, and then reflected by the spectral mirror 37 so as to be focused by the objective lens 38, to thereby irradiate a desired observation position on the observation object 39. At this time, the Galvano mirror 36 is driven to thereby sequentially scan pulse irradiation positions on the observation object 39.

Here, the observation object 39 is, for example, a human skin or a small laboratory animal such as a mouse. The observation object 39 generates two-photon fluorescence or produces second harmonic generation (SHG) when irradiated with short optical pulses.

The two-photon fluorescence or the second harmonic thus generated passes through the spectral mirror 37 via the objective lens 38, and then passes through the barrier filter 41 for cutting off stray light resulting from the short optical pulses, so as to be detected, as signal light, by the detector 42. The detector 42 is connected to an image processing device (not shown), together with the Galvano mirror 36, so that a two-dimensional microscope image can be formed based on the signal light intensity obtained by the detector 42 and the information on the short optical pulse irradiation position on the observation object 39.

With the above-mentioned configuration, hardly any non-linear optical effect is generated in the short optical pulse source 31 and in the short optical pulse delivery system. Further, the dispersion generator 35 compensates a second-order phase change in the spectrum of the short optical pulse source 31 and the total group-velocity dispersion in the optical system from the lens 32 to the observation object 39.

On the other hand, the group-velocity dispersion slope generated mainly in the hollow core photonic crystal fiber 33 or the like still remains uncompensated. More preferably, the conditions defined by Expressions (19), (20), and (21) are satisfied. Therefore, $\lambda_1$, $\lambda_2$ can be obtained from Expressions (2) and (3), so that a preferred range of the spectral width (full width at half maximum) of short optical pulses can be obtained based on Expression (1).

Figure 10:
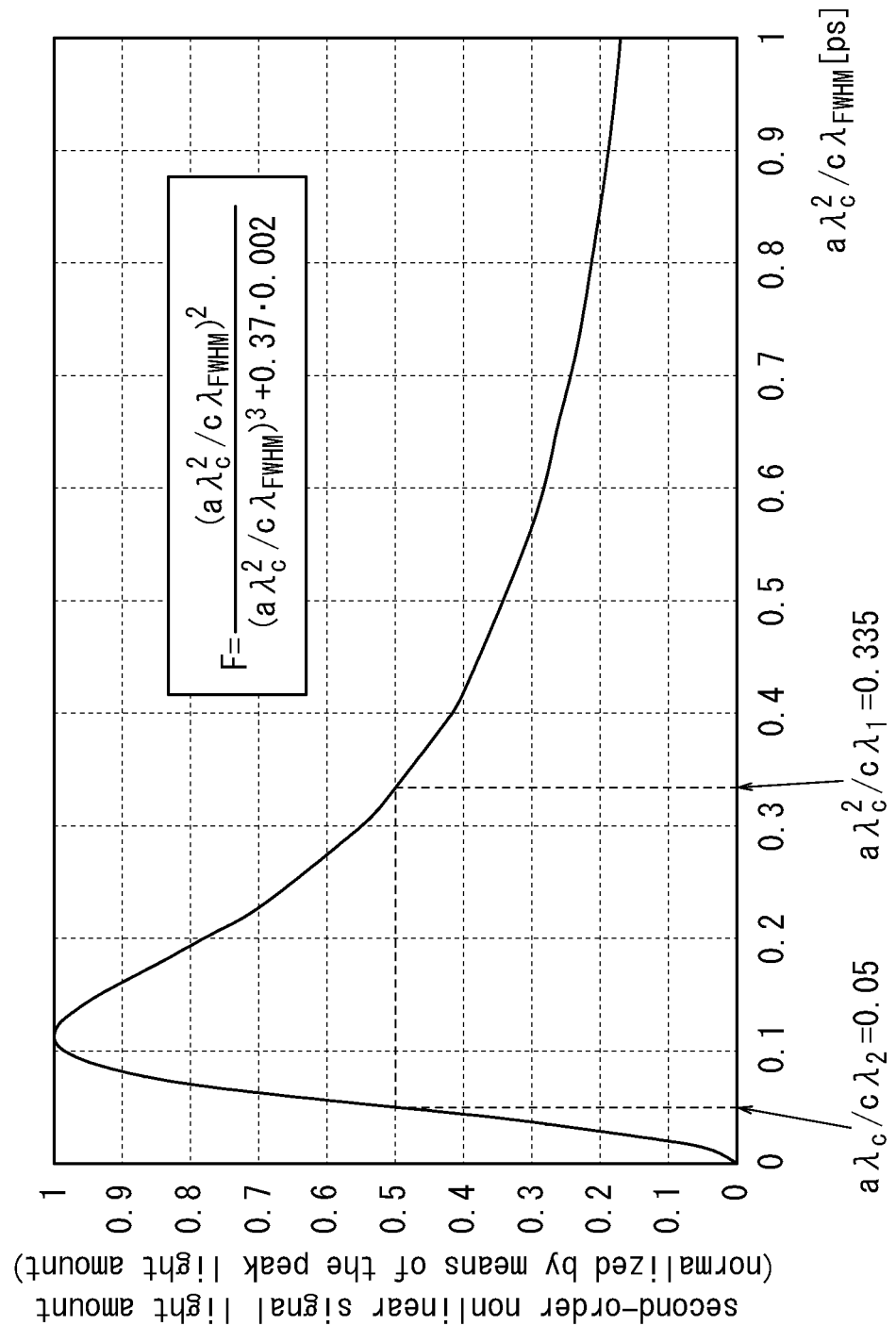
FIG. 10 is a graph showing a relation between the signal light amount generated by the second-order nonlinear optical effects and a spectral width of optical pulses emitted from a short optical pulse source according to the third embodiment.
Figure 11:
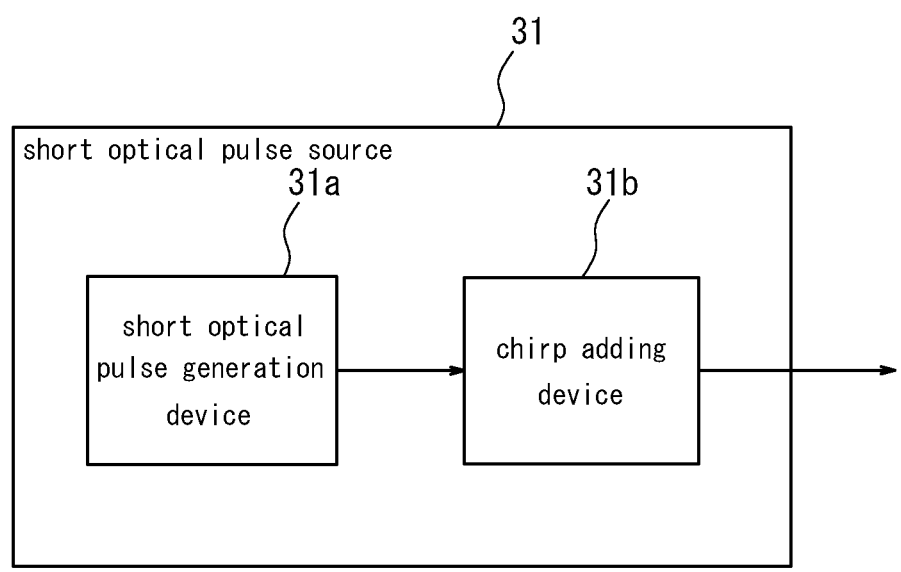
FIG. 11 is a configuration diagram of a short optical pulse source that includes, within the short optical pulse source, a chirp adding device.

FIG. 10 is a graph showing a relation between the signal light amount F generated by the second-order nonlinear optical effects and the parameter $a\lambda_c^2/c\lambda_{FWHM}$ of optical pulses emitted from the short optical pulse source, according to the third embodiment. As shown in the graph, optimal short optical pulses satisfy the range of $0.05 < a\lambda_c^2/c\lambda_{FWHM} < 0.335$, from which a range of the spectral width (full width at half maximum) of the optimal short optical pulses was obtained as follows:

$\lambda_1 = 3.3$ nm $\lambda_2 = 22.3$ nm.

Accordingly, for efficient generation of the second-order nonlinear optical effects in an observation object irradiated with short optical pulses, it is effective to use short optical pulses having a spectral width satisfying the following range:

3.3 nm $< \lambda_{FWHM} < 22.3$ nm.

The short optical pulses generated from the short optical pulse source 31 have a spectral width (full width at half maximum) of 11 nm, which falls within the above-mentioned range.

Short optical pulses immediately after being emitted from the short optical pulse source 31 have $T_{FWHM}$ and $f_{FWHM}$ calculated as follows:

$T_{FWHM} \times f_{FWHM} = 1.15$.

Accordingly, when the short optical pulses immediately after being emitted from the pulse source is extremely high in peak power, an optical element (such as a wavelength plate, which is not shown) disposed in the subsequent stage may suffer damage such as a burn in the anti-reflection coating thereof. In view of this, short optical pulses to be emitted from the source may be chirped in advance so as to be decreased its peak power, to thereby suppress the generation of damage.

This embodiment is similar to the first and second embodiments in that the short optical pulse source emits chirped short optical pulses. However, similar effects can be obtained even when the short optical pulses are emitted as Fourier transform limited pulses that have substantially no chirp, and hence the short optical pulse source may emit substantially unchirped short optical pulses.

In deriving the above-mentioned preferred range of $\lambda_{FWHM}$, assuming that the short optical pulse source 31 generates sech short optical pulses, parameters are defined as follows:

a=0.315, k=0.37, $D_{3d}$=0.002 ps³, and

α=0.5, which were assigned in Expressions (4) to (8), to thereby obtain $\lambda_{FWHM}$.

Here, similarly to the first embodiment, how to derive k and $D_{3d}$ is briefly described. First, k is a parameter depending on the waveform of short optical pulses, and can be factorized into two factors as $k = k_1 \times k_2$.

It indicates that the signal light amount F decreases along with the increase of $k_1$ when light sources different in pulse temporal width ($T_0$) at the Fourier transform limit are provided and pulses are made incident on an optical system having a group-velocity dispersion slope of $D_{3d}$, so as to estimate the signal light amount to be generated by the second-order nonlinear optical effects. Here, $k_1$ represents a coefficient at this time, which is obtained as $k_1 = 0.0676$ with sech short optical pulses.

Further, $k_2$ is the cube of a ratio between the full width at half maximum $T_{FWHM}$ of the waveform of short optical pulses and the width $T_0$ at which the signal intensity becomes 1/e, which are expressed as follows accordingly:

$$T_{FWHM} = \sqrt[3]{k_2} \cdot T_0 \qquad (29),$$

and $k_2$ is obtained as $1.763^3$ with sech pulses.

Therefore, k is calculated by multiplying $k_1$ by $k_2$, and obtained as 0.37.

Next, how to derive the value of the group-velocity dispersion slope $D_{3d}$ is described. $D_{3d}$ is obtained as a sum of $D_{3d1}$ generated from the hollow core photonic crystal fiber 33 and $D_{3d2}$ generated from the dispersion generator 35. As compared to the group-velocity dispersion slope generated from the hollow core photonic crystal fiber 33 or the like, the group-velocity dispersion slope generated from other components such as the lens 32 is extremely small enough to be negligible. Similarly, third or higher-order phase change in the spectrum of the short optical pulse source 31 can also be negligible.

Then, $D_{3d1}$ generated from the hollow core photonic crystal fiber 33 and $D_{3d2}$ generated from the dispersion generator are obtained as follows:

$D_{3d1}=0.003$ ps$^3$ $D_{3d2}=-0.001$ ps$^3$, and the total group-velocity dispersion slope $D_{3d}$ is obtained as follows:

$D_{3d}=0.002$ ps$^3$.

As described above, according to this embodiment, there is provided a microscope nonlinear optical device that includes a sech short optical pulse source and a short optical pulse delivery system, in which the spectral width (full width at half maximum) of short optical pulses generated from the short optical pulse source is adapted to satisfy the range of 3.3 nm$<\lambda_{FWHM}<$22.3 nm defined by Expression (1) that is obtained based on Expressions (2) to (8). Accordingly, the waveform distortion of optical pulses resulting from a group-velocity dispersion slope is alleviated so that it is possible to irradiate an object with short optical pulses having high peak power.

Further, when the conditions defined by Expressions (19), (20), (21) are satisfied, the nonlinear optical effects and the group-velocity dispersion effects in a nonlinear optical device are small enough to be negligible, and hence a waveform change resulting from the group-velocity dispersion slope prominently appears in short optical pulses. Thus, the use of ultrashort optical pulses with the above-mentioned temporal width is particularly effective.

Further, the dispersion generator 35 is provided for compensating a second-order phase change in the spectrum of the short optical pulse source 31 and the total group-velocity dispersion in the optical system from the lens 32 to the observation object 39, so that group-velocity dispersion generated in the nonlinear optical device such as the short optical pulse delivery system can be compensated. As a result, it is possible to irradiate short optical pulses having high peak power onto an object to be irradiated with short optical pulses, so that the nonlinear optical effects can be efficiently generated.

Although the short optical pulse source 31 generates chirped short optical pulses, the short optical pulse source 31 may also be configured by including: the short optical pulse generating device 31a for generating substantially unchirped short optical pulses; and a chirp adding device 31b for adding chirp to the substantially unchirped short optical pulses.

Although the dispersion generator 35 is disposed immediately after the lens 34 as illustrated in FIG. 8, the present invention is not limited thereto, and the dispersion generator 35 may be disposed at an arbitrary position in the short optical pulse delivery system.

Fourth Embodiment

Figure 12:
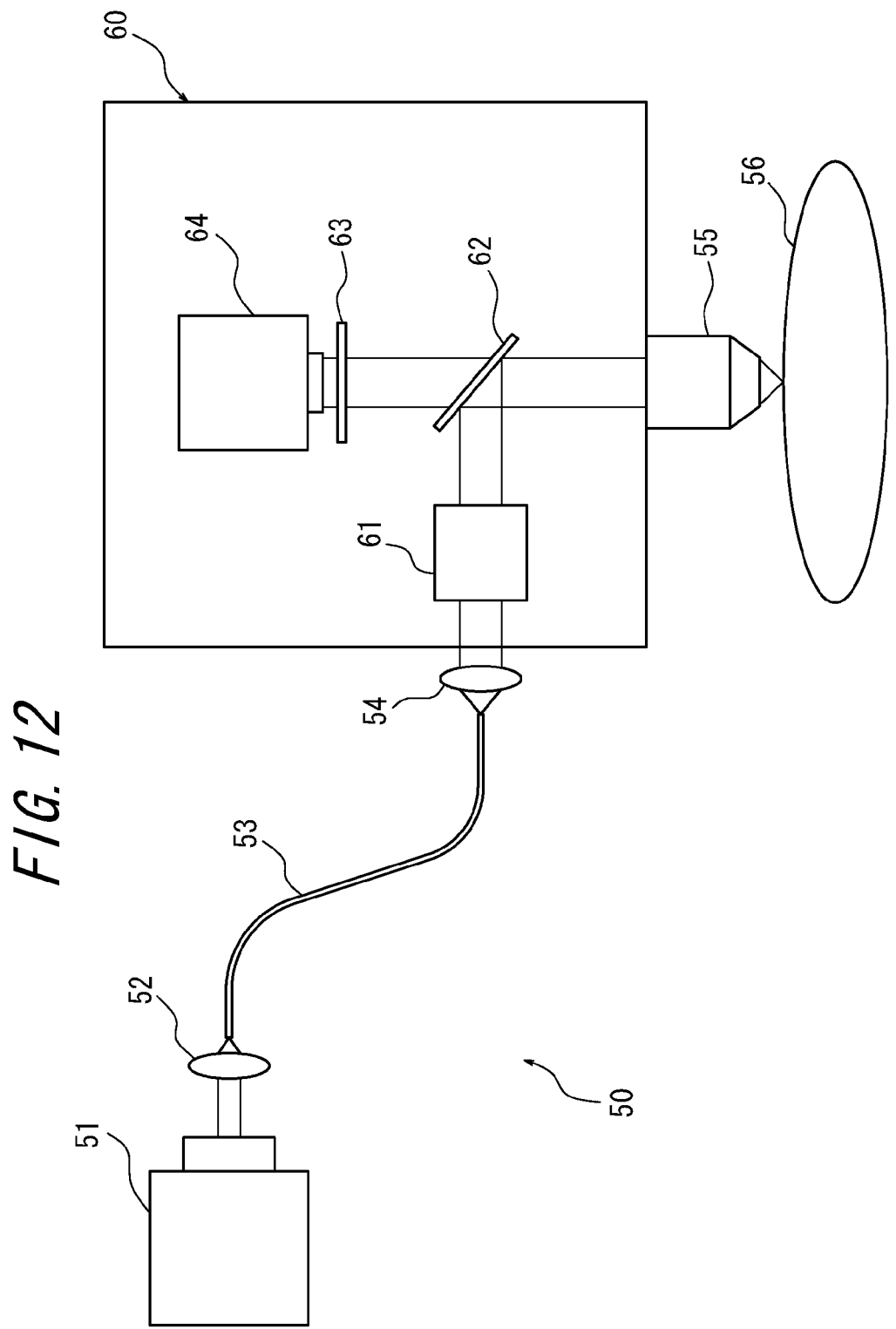
FIG. 12 is a schematic configuration diagram of a microscope nonlinear optical device according to a fourth embodiment of the present invention.

FIG. 12 is a schematic configuration diagram of a microscope nonlinear optical device 50 according to a fourth embodiment of the present invention.

The microscope nonlinear optical device is configured by including: a short optical pulse source 51 for generating sech short optical pulses; a lens 52; a hollow core photonic crystal fiber 53; a lens 54; a Galvano mirror 61; a spectral mirror 62; an objective lens 55; a barrier filter 63; and a detector 64. Of those, the Galvano mirror 61, the spectral mirror 62, the barrier filter 63, and the detector 64 are arranged within a microscope main body 60.

The short optical pulse source 51 is configured, for example, as a light source using a titanium: sapphire laser for generating sech short optical pulses having a wavelength of 1020 nm in the near-infrared region. The short optical pulse source 51 emits substantially unchirped short optical pulses, with an average power of 0.6 W, a repetition frequency of 80 MHz, a temporal width (full width at half maximum) of 120 fs, and a spectral width (full width at half maximum) of 9 nm.

Further, the short optical pulse source 51 is provided with a spectral width adjusting mechanism (not shown) for adjusting the spectral width, so that the short optical pulse source 51 is adjustable to a spectral width with which the nonlinear optical effects are most efficiently generated in an object to be irradiated with short optical pulses. The short optical pulse source 51 is adjusted in advance to a spectral width of 9 nm, which is an optimal value derived based on the group-velocity dispersion slope of the nonlinear optical device. Examples of the spectral width adjusting mechanism include a Pulse-Shaper as described in U.S. Pat. No. 7,430,071.

The lens 52, the hollow core photonic crystal fiber 53, the lens 54, the Galvano mirror 61, the spectral mirror 62, and the objective lens 55 form a short optical pulse system which delivers short optical pulses emitted from the short optical pulse source 51 to a living body as the observation object 56. Here, the spectral mirror 62 is a dichroic mirror that has frequency characteristics of passing short optical pulses delivered from the short optical pulse source 51 while reflecting signal light generated from the observation object 56 irradiated with short optical pulses.

Next, description is given of an operation of the microscope nonlinear optical device 50 in its entirety. Light emitted from the short optical pulse source 51 passes through the lens 52 so as to be incident on the hollow core photonic crystal fiber 53. The short optical pulses having exited from the hollow core photonic crystal fiber 53 are collimated by the lens 54, and then sequentially reflected by the Galvano mirror pair 61 and reflected by the spectral mirror 62 so as to be focused by the objective lens 55, to thereby irradiate a desired observation position on the observation object 56. At this time, the Galvano mirror 61 is driven to thereby sequentially scan pulse irradiation positions on the observation object 56.

Here, the observation object 56 is, for example, a human skin or a small laboratory animal such as a mouse. The observation object 56 generates two-photon fluorescence or produces second harmonic generation (SHG) when irradiated with short optical pulses.

The two-photon fluorescence or the second harmonic thus generated passes through the spectral mirror 62 via the objective lens 55, and then passes through the barrier filter 63 for cutting off stray light resulting from the short optical pulses, so as to be detected, as signal light, by the detector 64.

With the above-mentioned configuration, hardly any nonlinear optical effect is generated in the short optical pulse source 51 and in the short optical pulse delivery system, and the short optical pulse source 51 emits substantially unchirped short optical pulses.

Further, the wavelength is selected so as to reduce to substantially zero the group-velocity dispersion in the nonlinear optical device 50. Specifically, the wavelength is selected so that the sum of the amount of positive group-velocity dispersion generated in the objective lens 55 or the like and the amount of negative group-velocity dispersion generated in the hollow core photonic crystal fiber 53 becomes exactly zero.

Accordingly, the group-velocity dispersion $D_{2d1}$ generated from the hollow core photonic crystal fiber 53 and $D_{2d2}$ generated from the objective lens or the like are obtained as follows:

$D_{2d1}=-0.03$ ps$^2$ $D_{2d2}=0.03$ ps$^2$, and the total group-velocity dispersion $D_{2d}$ is obtained as follows:

$$D_{2d}=D_{2d1}+D_{2d2}=0.0 \text{ ps}^2.$$

Therefore, the amount of group-velocity dispersion can be reduced to zero in the nonlinear optical device without the need for a complicated mechanism such as a dispersion generator.

On the other hand, the group-velocity dispersion slope generated mainly in the hollow core photonic crystal fiber 53 or the like still remains uncompensated. More preferably, the conditions defined by Expressions (19), (20), and (21) are satisfied. Therefore, $\lambda_1, \lambda_2$ can be obtained from Expressions (2) and (3), so that a preferred range of the spectral width (full width at half maximum) of short optical pulses can be obtained based on Expression (1).

Figure 13:
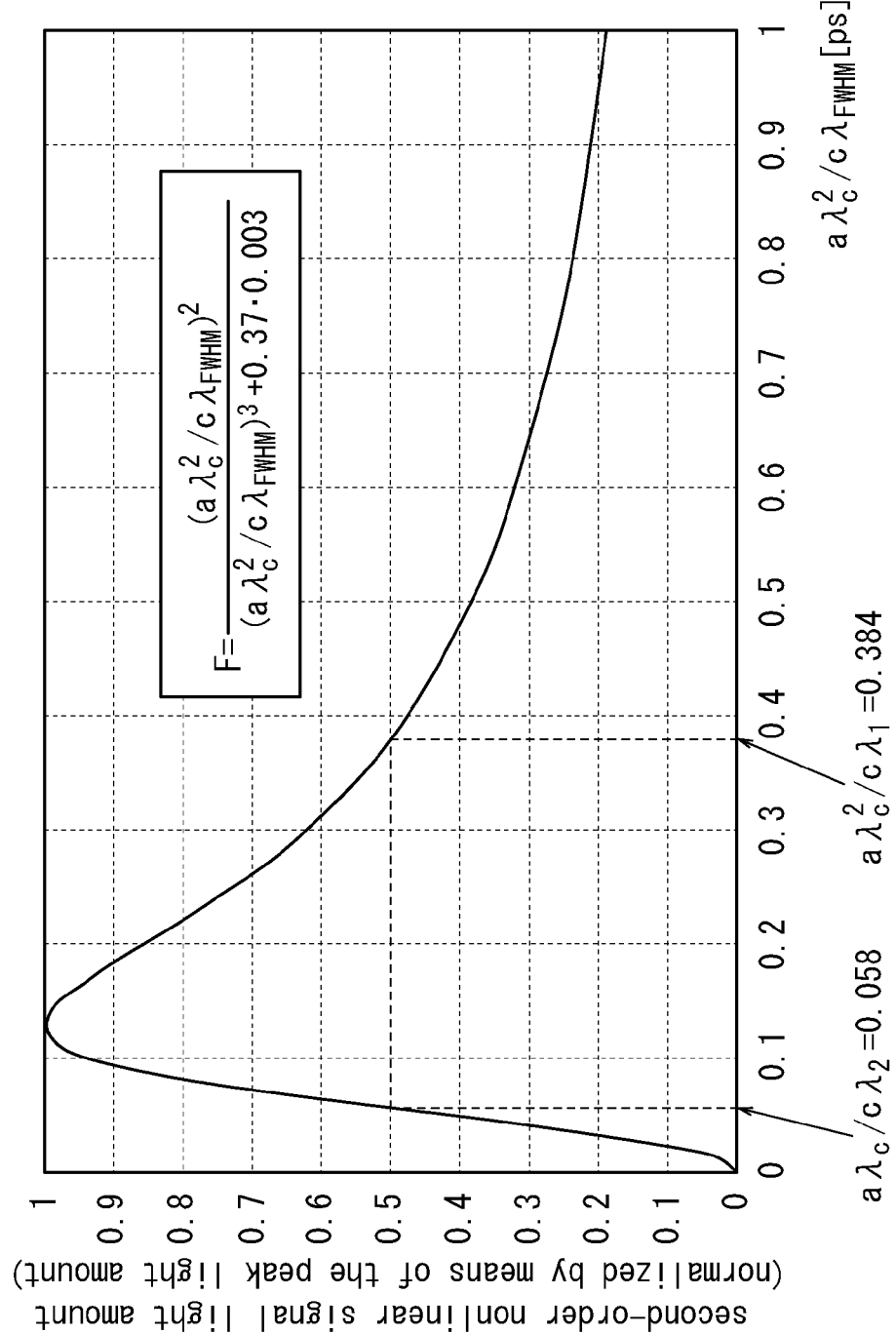
FIG. 13 is a graph showing a relation between the signal light amount generated by the second-order nonlinear optical effects and a spectral width of optical pulses emitted from a short optical pulse source according to the fourth embodiment.

FIG. 13 is a graph showing a relation between the signal light amount F generated by the second-order nonlinear optical effects and the parameter $a\lambda_c^2/c\lambda_{FWHM}$ of optical pulses emitted from the short optical pulse source, according to the fourth embodiment. As shown in the graph, optimal short optical pulses satisfy the range of $0.058<a\lambda_c^2/c\lambda_{FWHM}<0.384$, from which a range of the spectral width (full width at half maximum) of the optimal short optical pulses was obtained as follows:

$$\lambda_1=2.8 \text{ nm}$$

$$\lambda_2=18.8 \text{ nm}.$$

Accordingly, for efficient generation of the second-order nonlinear optical effects in an observation object irradiated with short optical pulses, it is effective to use short optical pulses having a spectral width satisfying the following range:

$$2.8 \text{ nm}<\lambda_{FWHM}<18.8 \text{ nm}.$$

The short optical pulses generated from the short optical pulse source 51 have a spectral width (full width at half maximum) of 9 nm, which falls within the above-mentioned range.

Short optical pulses immediately after being emitted from the short optical pulse source 51 have $T_{FWHM}$ and $f_{FWHM}$ calculated as follows:
$T_{FWHM} \times f_{FWHM}=0.315$, which means that an optimal spectral width can also be obtained, similarly to the first to third embodiments, even for unchirped short optical pulses.

In deriving the above-mentioned preferred range of $\lambda_{FWHM}$, assuming that the short optical pulse source 51 generates sech short optical pulses, parameters are defined as follows:
a=0.315,
k=0.37,
$D_{3d}$=0.002 ps³, and
α=0.5,
which are assigned in Expressions (4) to (8), similarly to the first embodiment, to thereby obtain $\lambda_{FWHM}$.

As described above, according to this embodiment, there is provided a microscope nonlinear optical device that includes a sech short optical pulse source and a short optical pulse delivery system, in which the spectral width (full width at half maximum) of short optical pulses generated from the short optical pulse source is adapted to satisfy the range of 2.8 nm<$\lambda_{FWHM}$<18.8 nm defined by Expression (1) which is obtained based on Expressions (2) to (8). As a result, the waveform distortion of optical pulses resulting from a group-velocity dispersion slope is alleviated so that it is possible to irradiate an object with short optical pulses having high peak power.

Further, the spectral width adjustment mechanism is provided, making it possible to set an optimal spectral width calculated based on the total group-velocity dispersion slope in the nonlinear optical device so as to efficiently generate nonlinear optical effects. Accordingly, short optical pulses with higher peak power can be irradiated onto an object.

In the fifth to eighth embodiments described below, the short optical pulse source 1 is adapted to generate short optical pulses close to the Fourier transform limit (hereinafter, referred to as transform limit) satisfying Expression (22). When $T_{FWHM} \cdot f_{FWHM}$ exceeds 0.88, signal light resulting from the second-order nonlinear optical effects generated in an object irradiated with the short optical pulses is decreased to approximately less than half of a perfect transform limit.

Here, $T_{FWHM} \cdot f_{FWHM}$ is calculated using the following expression, in which the spectral width is converted into a wavelength width.

$$T_{FWHM} \cdot f_{FWHM} = T_{FWHM} \cdot \left(\frac{c\lambda_{FWHM}}{\lambda_c^2}\right), \tag{30}$$

where c represents the speed of light, $\lambda_c$ represents the central wavelength of the short optical pulses, and $\lambda_{FWHM}$ represents a wavelength width (full width at half maximum).

Under the above-mentioned conditions, first, with no consideration given to the total amount of group-velocity dispersion slope in the short optical pulse delivery system, the signal light amount $F_{noD}$ [W], which is generated by the second-order nonlinear optical effects in an object irradiated with the short optical pulses, is expressed as Expression (31) below as shown in the left side of Expression (23).

$$F_{noD} = \frac{A \cdot P_{ave}^2}{f_{rep} \cdot T_{FWHM}}, \tag{31}$$

where A is a coefficient of an order of [1/W], $P_{ave}$ represents an average power of the short optical pulses per unit time, $f_{rep}$ represents a repetition frequency of the short optical pulses, and $T_{FWHM}$ represents the temporal width (full width at half maximum) of the short optical pulses.

The expression (31) shows that the signal light amount $F_{noD}$ generated by the second-order nonlinear optical effects in the object is higher when the temporal width of the short optical pulses is shorter. However, with consideration given to the total amount of group-velocity dispersion slope in the short optical pulse delivery system, the signal light amount $F_{noD}$ is obtained by multiplying Expression (31) by Expression (32) below, under the influence of the waveform deformation of the short optical pulses.

$$\frac{T_{FWHM}^3}{T_{FWHM}^3 + k \cdot D_{3d}} \tag{32}$$

where k is a parameter determined by the waveform of the short optical pulses, and $D_{3d}$ represents the total amount of group-velocity dispersion slope.

The signal light amount F generated by the second-order nonlinear optical effects in an object irradiated with the short optical pulses is expressed as Expression (33) below obtained by multiplying Expression (31) by Expression (32).

$$F = \frac{A \cdot P_{ave}^2}{f_{rep}} \cdot \frac{T_{FWHM}^2}{T_{FWHM}^3 + k \cdot D_{3d}} \quad (33)$$

Figure 14:
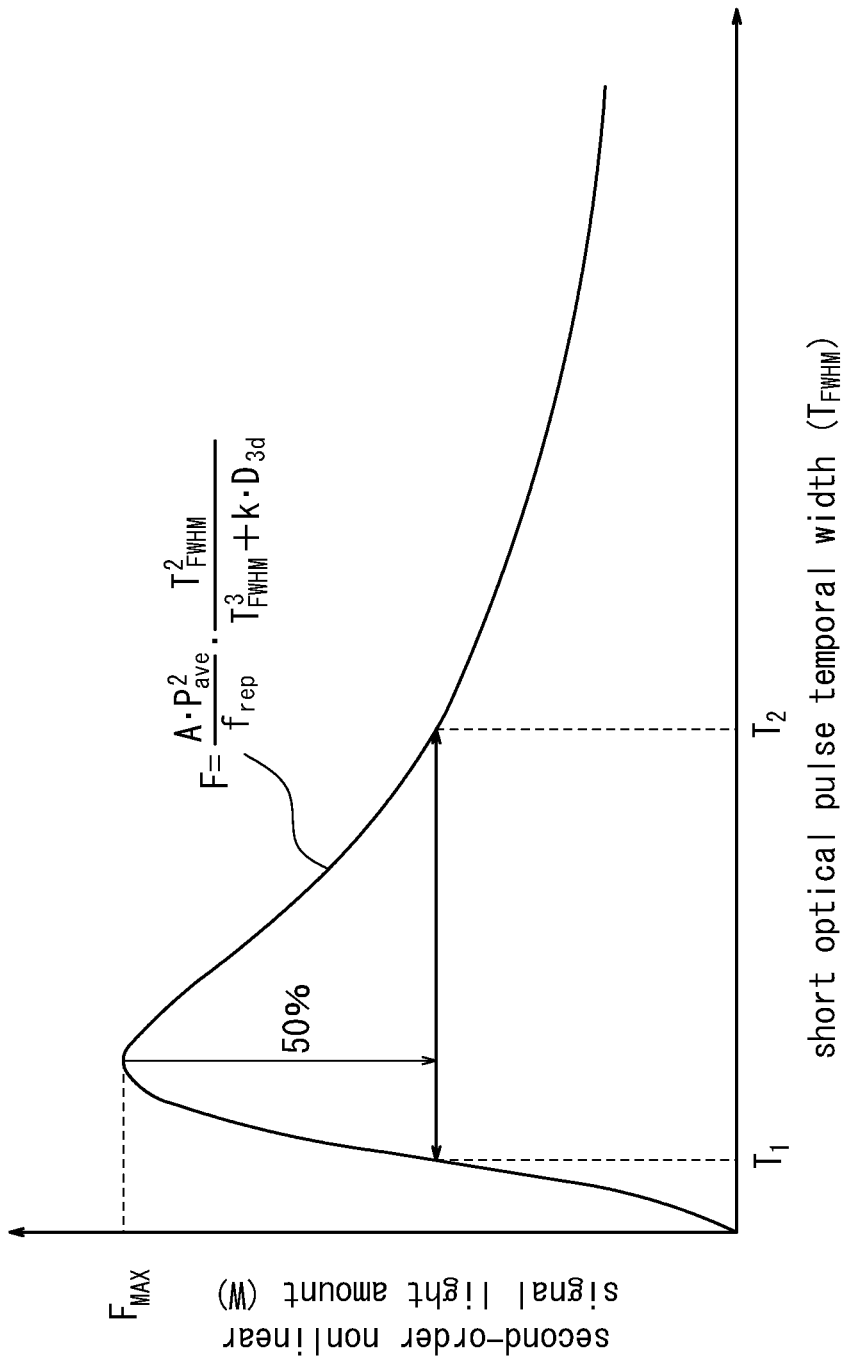
FIG. 14 is a graph showing a relation between the signal light amount generated by the second-order nonlinear optical effects and a pulse temporal width of optical pulses emitted from a short optical pulse.

FIG. 14 shows Expression (33) in a graph which has the short optical pulse width $T_{FWHM}$ on abscissa. As shown in FIG. 14, in the case where the total amount of group-velocity dispersion slope in the short optical pulse delivery system is too large to be negligible, the signal light amount F resulting from the second-order nonlinear optical effects generated in an object irradiated with short optical pulses becomes substantially maximum ($F_{MAX}$) when the short optical pulses fall within a certain temporal range. The signal light amount F resulting from the second-order nonlinear optical effects significantly decreases when the short optical pulses have a temporal width that greatly falls out of the range.

Here, in view of the fluorescence intensity in two-photon fluorescence observation and thermal damage to an object irradiated with short optical pulses, it is preferred to use short optical pulses having $T_{FWHM}$ that falls within a range ($T_1 < T_{FWHM} < T_2$) in which the signal light amount F generated by the second-order nonlinear optical effects decreases from its highest value ($F_{MAX}$) to 50% ($\alpha$=0.5) thereof. Further, in view of the sensitivity of the detector, it is preferred to use short optical pulses having $T_{FWHM}$ that falls within a range in which the signal light amount F to be generated is 60% or more of its highest value ($F_{MAX}$), and more preferably 70% or more depending on the observation object. For detecting weak signals, it is further preferred that $T_{FWHM}$ fall within a range in which the signal light amount F to be generated is 80% or more of its highest value.

The parameters $T_1$, $T_2$ defining the range of the optimal pulse temporal width $T_{FWHM}$ described above are obtained from Expression (33), so that Expressions (14) and (15) below can be obtained.

$$T_1 = 2\sqrt{-p} \cos\left(\frac{u}{3} + \frac{4\pi}{3}\right) + \frac{(kD_{3rd})^{1/3}}{\alpha \cdot 2^{2/3}}, \quad (14)$$

$$T_2 = 2\sqrt{-p} \cos\left(\frac{u}{3}\right) + \frac{(kD_{3rd})^{1/3}}{\alpha \cdot 2^{2/3}}, \quad (15)$$

where k is a parameter that varies depending on the waveform of the short optical pulses, which is given as 0.535 when the pulses have a Gaussian waveform and as 0.370 when the pulses have a hyperbolic secant (sech) waveform. The parameter k takes an intermediate value between those two values when the pulses have a waveform intermediate between the Gaussian and the sech.

Therefore, in the nonlinear optical device according to the present invention, the spectral width $T_{FWHM}$ is defined so as to satisfy the above-mentioned requirements, so that the influences of temporal broadening and waveform distortion of optical pulses resulting from the group-velocity dispersion slope can be alleviated without the need for a mechanism for compensating the group-velocity dispersion slope, to thereby irradiate an object with short optical pulses having high peak power.

In the following, the fifth to eighth embodiments of the present invention are described.

Fifth Embodiment

Figure 15:
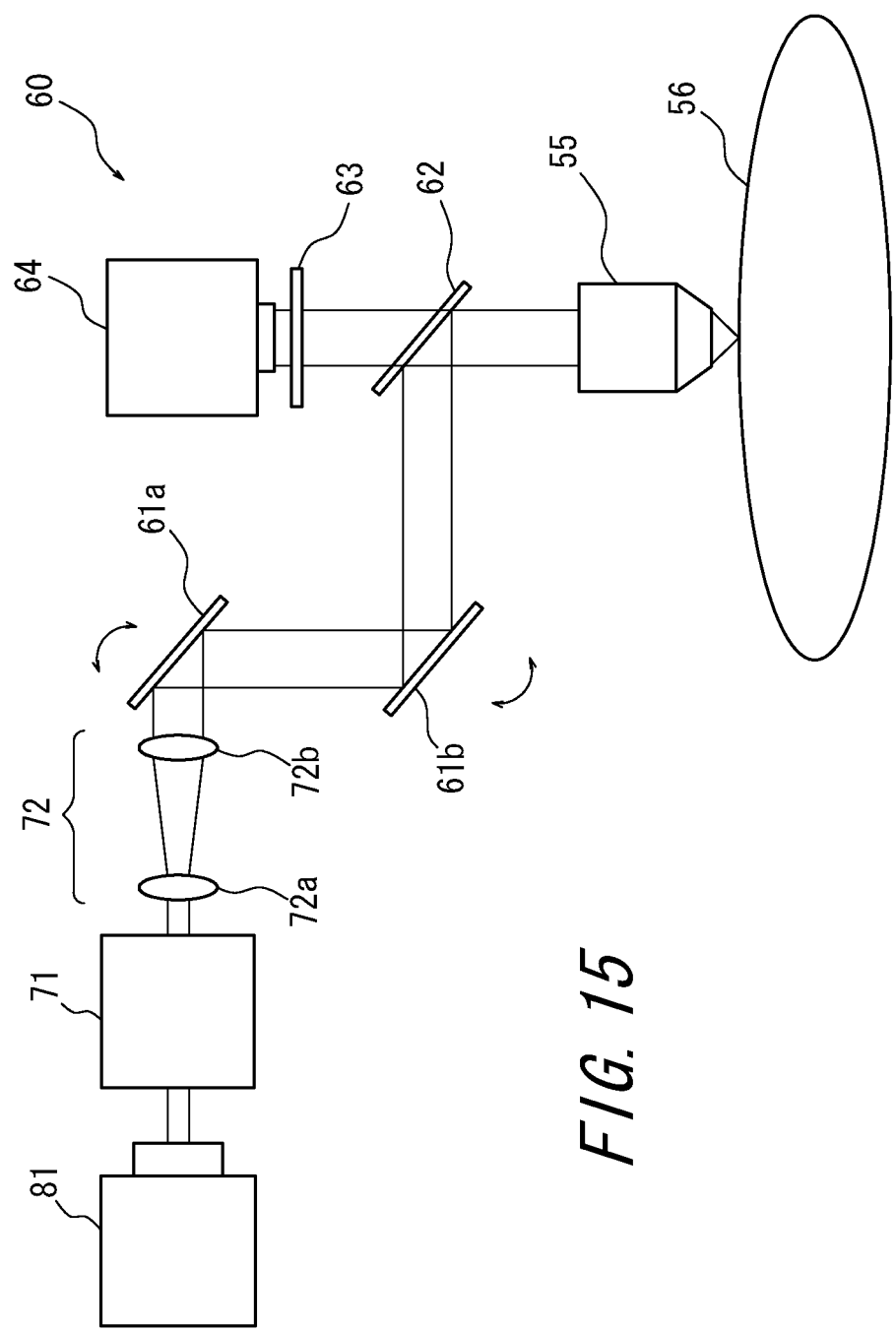
FIG. 15 is a schematic configuration diagram of a multiphoton microscope according to a fifth embodiment of the present invention.

FIG. 15 is a schematic configuration diagram of a multiphoton microscope according to the fifth embodiment of the present invention.

The multiphoton microscope is configured by including: a short optical pulse source 81 for generating unchirped sech short optical pulses; a group-velocity dispersion compensation device 71; a beam expander 72; Galvano mirrors 61a, 61b; a spectral mirror 62; an objective lens 55; a barrier filter 63; and a detector 64. Components similar to those of the fourth embodiment are denoted by the same reference symbols.

The short optical pulse source 81 is configured, for example, as a light source using a titanium: sapphire laser for generating sech short optical pulses having a wavelength of 980 nm in the near-infrared region. The short optical pulse source 81 emits chirped short optical pulses, with an average power of 1 W, a repetition frequency of 80 MHz, a temporal width (full width at half maximum) of 80 fs, and a spectral width (full width at half maximum) of 13 nm.

The group-velocity dispersion compensation device 71, the beam expander 72, the Galvano mirrors 61a, 61b, the spectral mirror 62, and the objective lens 55 form a short optical pulse delivery system for delivering short optical pulses emitted from the short optical pulse source 81 to the observation object 56 to be observed.

Figure 16:
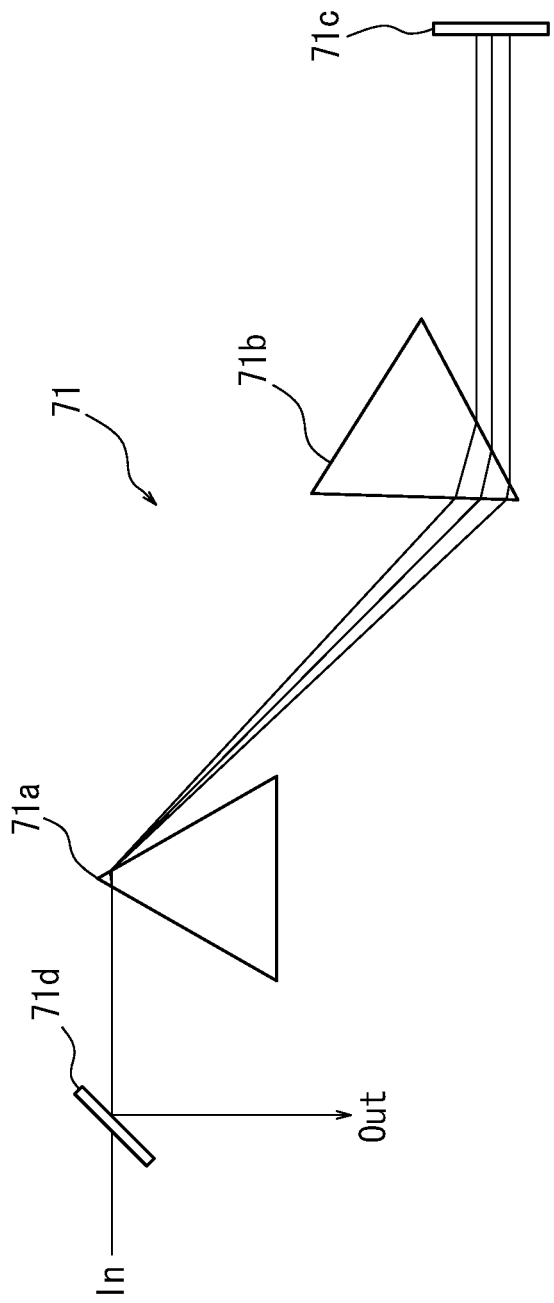
FIG. 16 is a configuration diagram illustrating an example of a group-velocity dispersion compensation device of FIG. 15.

The group velocity dispersion compensation device 71 is a device for compensating the total amount of group-velocity dispersion in the optical system from the short optical pulse source 81 to the observation object 56. The group-velocity dispersion compensation device 71 is known as the one using, for example, a prism pair, which includes prisms 71a, 71b and mirrors 71c, 71d as illustrated in FIG. 16. The distance between the prisms 71a and 71b is about 75 cm, and the prisms thus employed are Brewster prisms formed of a glass material such as SF58.

An operation of the group-velocity dispersion compensation device 71 of FIG. 16 is briefly described. The short optical pulses emitted from the short optical pulse source 81 are incident on the prism 71a. When passing through the prism 71a, the short optical pulses are subjected to angular dispersion depending on the refractive index dispersion of the glass. Further, the short optical pulses broadened by the angular dispersion pass through the prism 71b so as to be collimated, which are reflected by the mirror 71c. The light thus reflected passes through the prisms 71b, 71a so as to be reflected by the mirror 71d, and then exits therefrom. As a result, a negative group-velocity dispersion is generated, which compensates the group-velocity dispersion in the nonlinear optical device.

Next, description is given of an operation of the multiphoton microscope in its entirety. Light emitted from the short optical pulse source 81 passes through the group-velocity dispersion compensation device 71, and is expanded in beam diameter by the beam expander 71 formed of lenses 72a and 72b. The short optical pulses having exited from the beam expander 72 are sequentially reflected by the Galvano mirrors 61a and 61b, and then reflected by the spectral mirror 62. The operations thereafter in the microscope main body 50 are similar to those of the fourth embodiment.

With the above-mentioned configuration, hardly any nonlinear optical effect is generated in the short optical pulse source 81 and in the short optical pulse delivery system, and the group-velocity dispersion generated in components such as the beam expander 72 and the objective lens 55 is compensated by the group-velocity dispersion compensation device 71. On the other hand, the group-velocity dispersion slope still remains uncompensated. More preferably, the conditions defined by Expressions (19), (20), and (21) are satisfied. Therefore, $T_1$, $T_2$ can be obtained from Expressions (14) and (15), so that a preferred temporal width (full width at half maximum) of short optical pulses can be obtained based on Expression (13).

Figure 17:
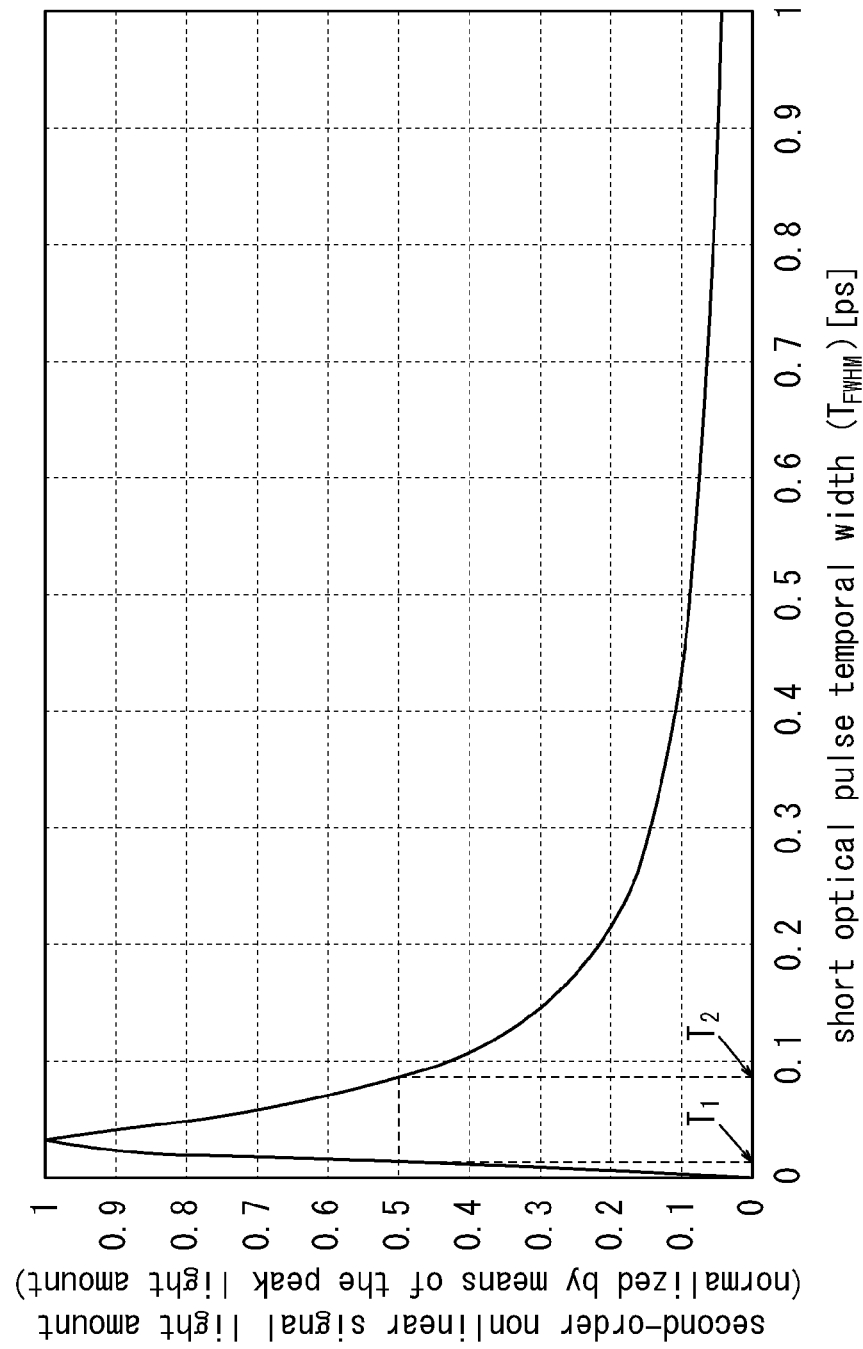
FIG. 17 is a graph showing a relation between the signal light amount generated by the second-order nonlinear optical effects and a pulse temporal width of optical pulses emitted from a short optical pulse source according to the fifth embodiment.

FIG. 17 is a graph showing a relation between the signal light amount F generated by the second-order nonlinear optical effects and a pulse temporal width $T_{FWHM}$ of optical pulses emitted from the short optical pulse source 81 according to the fifth embodiment. The range of an optimal temporal width (full width at half maximum) of short optical pulses was obtained as follows:

$$T_1 = 12 \text{ [fs]}$$

$$T_2 = 83 \text{ [fs]}.$$

Accordingly, for efficient generation of the second-order nonlinear optical effects in an observation object irradiated with short optical pulses, it is effective to use short optical pulses having a temporal width satisfying the following range:

$$12 \text{ [fs]} < T_{FWHM} < 83 \text{ [fs]}.$$

The short optical pulses generated from the short optical pulse source 81 have a temporal width (full width at half maximum) of 80 [fs], which falls within the above-mentioned range.

Short optical pulses immediately after being emitted from the short optical pulse source 81 have $T_{FWHM}$ and $f_{FWHM}$ calculated as follows:
$T_{FWHM} \times f_{FWHM} = 0.33$, which satisfies the condition defined by Expression (22).

In deriving the above-mentioned preferred range of $T_{FWHM}$, assuming that the short optical pulse source 81 generates sech short optical pulses, parameters are defined as follows:
k=0.37,
$D_{3d}$=0.00003 [ps$^3$], and
α=0.5.

Here, $D_{3d}$ is obtained as a sum of $D_{3d1}$ generated from lenses such as the beam expander 72 and $D_{3d2}$ generated from the group-velocity dispersion compensation device (prism pair) 71. $D_{3d1}$ is obtained from Sellmeier equation rendering the wavelength dependence of the refractive index of the lens material being used, and $D_{3d2}$ is calculated from the expression for estimating a group-velocity dispersion slope resulting from a prism pair, which is described in an article "R. L. Fork, O. E. Martinez, and J. p. Gordon, 'Negative dispersion using pairs of prisms,' Opt. Lett., 9, pp. 150 (1984)".

As described above, according to this embodiment, there is provided a nonlinear optical device that includes a sech short optical pulse source and a short optical pulse delivery system, in which the broadening of short optical pulses due to the waveform deformation resulting from the group-velocity dispersion slope generated in the device is larger than the broadening of short optical pulses due to the waveform deformation resulting from the nonlinear optical effects and the group-velocity dispersion generated in the device, and the short optical pulses generated by the short optical pulse source have a temporal width (full width at half maximum) that is defined to satisfy $12 \text{ [fs]} < T_{FWHM} < 83 \text{ [fs]}$. As a result, the temporal broadening and waveform distortion of optical pulses resulting from a group-velocity dispersion slope are alleviated so that it is possible to irradiate an object with short optical pulses having high peak power.

Further, when the conditions defined by Expressions (19), (20), (21) are satisfied, the nonlinear optical effects and the group-velocity dispersion effects in the nonlinear optical device are small enough to be negligible, and hence a waveform change resulting from the group-velocity dispersion slope prominently appears in short optical pulses. Thus, the use of ultrashort optical pulses with the above-mentioned temporal width is particularly effective.

Although the group-velocity dispersion compensation device 71 is disposed immediately after the short optical pulse source, the present invention is not limited thereto. The group-velocity dispersion compensation device may be disposed at an arbitrary position in the short optical pulse delivery system in order to compensate the total group-velocity dispersion. Further, the group-velocity dispersion compensation device is not limited to the one that uses a prism pair, and there may be employed various devices for compensating the group-velocity dispersion, such as a device using a diffraction grating pair (similarly to the dispersion generator of the third embodiment).

Sixth Embodiment

Figure 18:
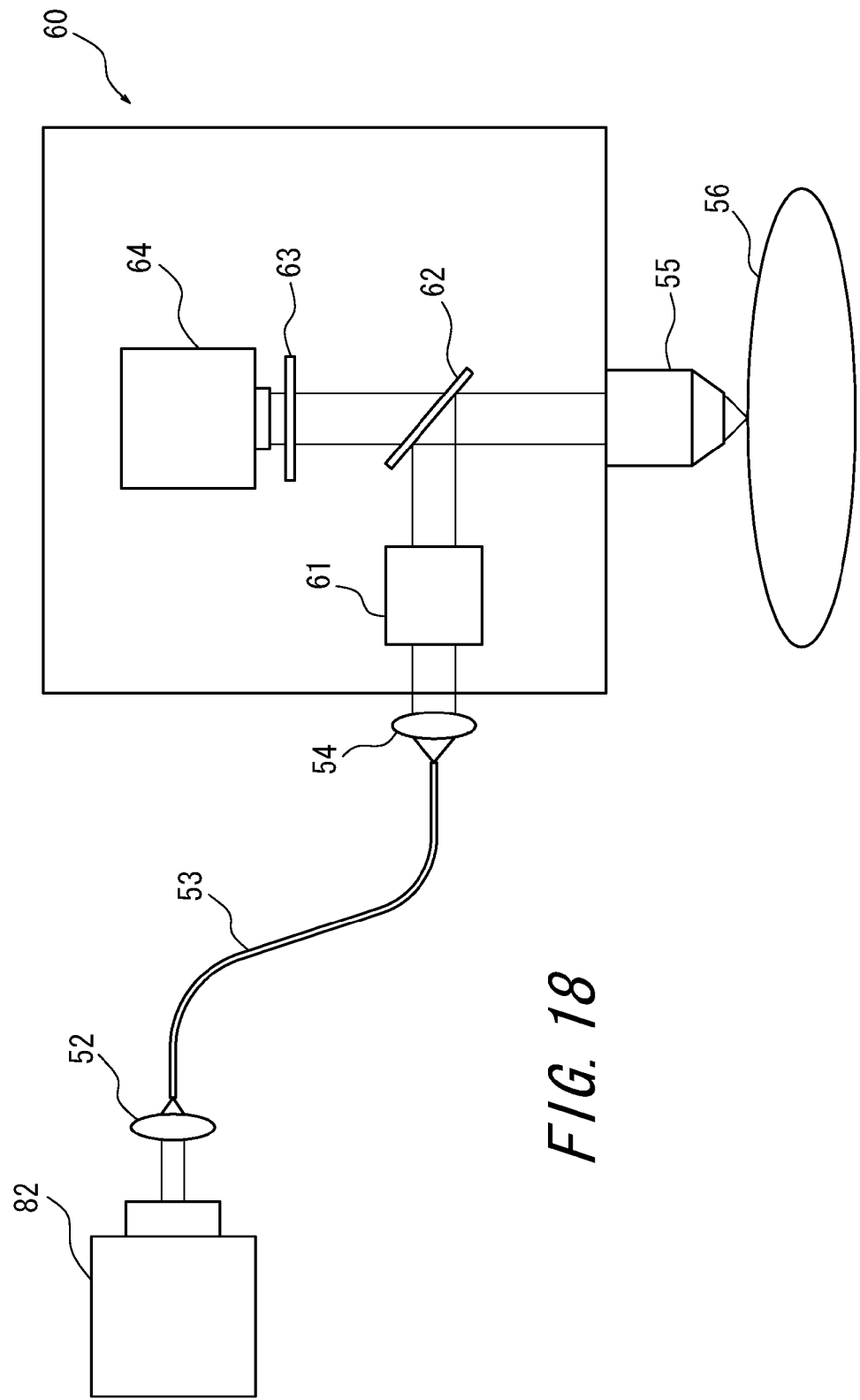
FIG. 18 is a schematic configuration diagram of a multiphoton microscope according to a sixth embodiment of the present invention.

FIG. 18 is schematic configuration diagram of a multiphoton microscope according to a sixth embodiment of the present invention. In this embodiment, the present invention is applied to a conventional multiphoton microscope.

The multiphoton microscope is configured by including: a short optical pulse source 82 which generates unchirped Gaussian short optical pulses; a lens 52; a hollow core photonic crystal fiber 53; a lens 54; and a conventional microscope device 60.

The short optical pulse source 82 is configured, for example, as a light source using a titanium: sapphire laser for generating Gaussian short optical pulses having a wavelength of 980 nm in the near-infrared region, with an average power of 1 W, a repetition frequency of 80 MHz, a temporal width (full width at half maximum) of 148 fs, and a spectral width of 15 nm.

Short optical pulses emitted from the short optical pulse source 82 are incident on, by means of the lens 52, the hollow core photonic crystal fiber 53 which is 3 m in length, so as to be delivered through the hollow core photonic crystal fiber 53, and then supplied, as a collimated beam, to the microscope device 60 by means of the lens 54. In general, the amount of group-velocity dispersion and the amount of group-velocity dispersion slope in a hollow core photonic crystal fiber are extremely large, whereas the amount of group-velocity dispersion can be reduced to zero by selecting the wavelength of light to be delivered therethrough. In the hollow core photonic crystal fiber 53 employed for this embodiment, the amount of group-velocity dispersion is reduced to zero when the short optical pulses generated by the short optical pulse source 82 have a wavelength of 980 nm.

The microscope main body 60 is configured by including: a Galvano mirror pair 61; a spectral mirror 62; an objective lens 55; a barrier filter 63; and a detector 64. The Galvano mirror pair 61 includes two Galvano mirrors for scanning the observation object 56, which are similar in configuration and effect to the two Galvano mirrors 61a and 61b in the fifth embodiment. Further, the rest of the configuration in the microscope main body 60 is similar to those of the fourth to fifth embodiments, and hence the same components are denoted by the same reference symbols and the description thereof is omitted.

The lens 52, the hollow core photonic crystal fiber 53, the lens 54, the Galvano mirror pair 61, the spectral mirror 62, and the objective lens 55 form a short optical pulse delivery system.

With the above-mentioned configuration, the hollow core photonic crystal fiber 53 is used to connect between the short optical pulse source 82 and the microscope device 60, so that the short optical pulse source 82 can be disposed away from the microscope device 60. Such an arrangement significantly improves usability as compared to the fifth embodiment in which short optical pulses from the short optical pulse source 82 are propagated through space to be introduced into the microscope main body 60, because there is no need to realign the short optical pulse source 82 even after it has been moved.

Further, with the above-mentioned configuration, hardly any nonlinear optical effect is generated in the short optical pulse source 82 and in the short optical pulse delivery system. Meanwhile, in the hollow core photonic crystal fiber 53, no group-velocity dispersion is generated whereas a large group-dispersion slope is generated. In this case, the conditions defined by Expressions (19), (20), and (21) are preferably satisfied. Accordingly, based on $T_1$, $T_2$ obtained from Expressions (14) and (15), a preferred temporal width (full width at half maximum) of short optical pulses can be obtained from Expression (13).

Figure 19:
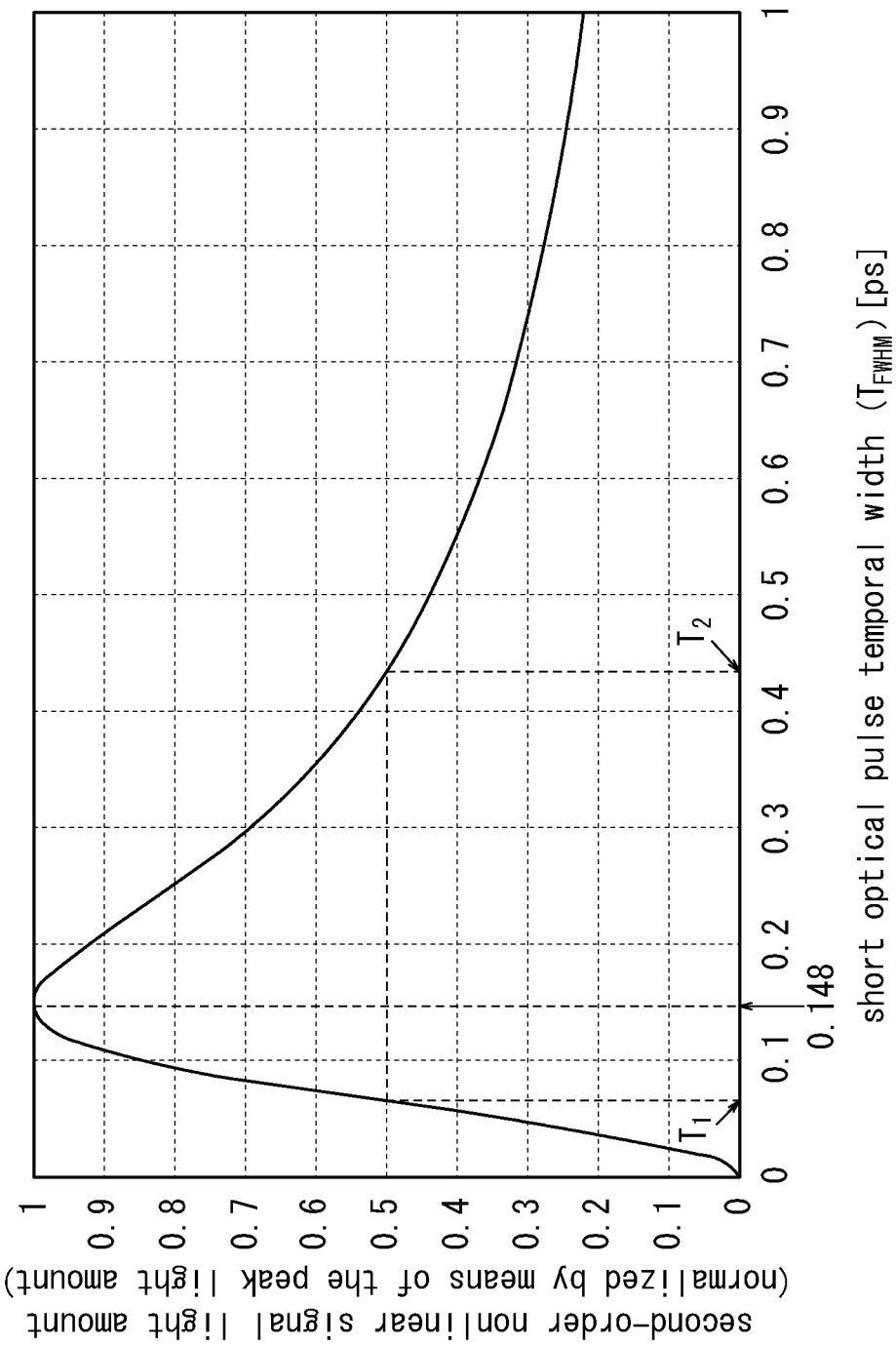
FIG. 19 is a graph showing a relation between the signal light amount generated by the second-order nonlinear optical effects and a pulse temporal width of optical pulses emitted from a short optical pulse source according to the sixth embodiment.

FIG. 19 is a graph showing a relation between the signal light amount F generated by the second-order nonlinear optical effects and a pulse temporal width $T_{FWHM}$ of optical pulses emitted from the short optical pulse source according to the sixth embodiment. The range of an optimal temporal width (full width at half maximum) of short optical pulses was obtained as follows:

$T_1$=65 [fs]

$T_2$=434 [fs].

Accordingly, for efficient generation of the second-order nonlinear optical effects in an observation object irradiated with short optical pulses, it is effective to use short optical pulses having a temporal width satisfying the following range:

65 [fs]<$T_{FWHM}$<434 [fs].

Further, a most preferred temporal width (full width at half maximum) of short optical pulses is 148 [fs], which means that the short optical pulses emitted from the short optical pulse source 82 of this embodiment have a temporal width (full width at half maximum) that is appropriate in value.

Further, short optical pulses immediately after being emitted from the short optical pulse source 82 have $T_{FWHM}$ and $f_{FWHM}$ calculated as $T_{FWHM} \times f_{FWHM}$=0.7, which satisfies the condition defined by Expression (22).

In deriving the above-mentioned preferred range of $T_{FWHM}$, assuming that the short optical pulse source 82 generates Gaussian short optical pulses, parameters were defined as follows:
k=0.535,
$D_{3d}$=0.003 [ps$^3$], and
α=0.5.

Here, the group-velocity dispersion slope $D_{3d}$ was calculated from known Expression (34), using the dispersion slope D (of approximately 4.4 [ps/nm$^2$/km]) at the zero dispersion wavelength of the hollow core photonic crystal fiber and assuming that the hollow core photonic crystal fiber has a length L=3 m, $$D_{3d} = \frac{\lambda^3}{(2\pi c)^2}\left(2D + \lambda\frac{dD}{d\lambda}\right) \cdot L \quad (34)$$

As described above, according to this embodiment, there is provided a nonlinear optical device that includes a Gaussian short optical pulse source and a short optical pulse delivery system, in which the broadening of short optical pulses due to the waveform deformation resulting from the group-velocity dispersion slope generated in the device is larger than the broadening of short optical pulses due to the waveform deformation resulting from the nonlinear optical effects and the group-velocity dispersion generated in the device, and the short optical pulses generated by the short optical pulse source have a spectral width (full width at half maximum) that is defined to satisfy 65 [fs]<$T_{FWHM}$<434 [fs]. As a result, the temporal broadening and the waveform distortion of optical pulses resulting from a group-velocity dispersion slope are alleviated so that it is possible to irradiate an object with short optical pulses having high peak power.

Further, when the conditions defined by Expressions (19), (20), (21) are satisfied, the nonlinear optical effects and the group-velocity dispersion effects in the nonlinear optical device are small enough to be negligible, and hence a waveform change resulting from the group-velocity dispersion slope prominently appears in short optical pulses. Thus, the use of ultrashort optical pulses with the above-mentioned temporal width is particularly effective.

Unlike in the fifth embodiment, this embodiment does not employ the group-velocity dispersion compensation device, because the hollow core photonic crystal fiber used in this embodiment is free from group-velocity dispersion. In the event that there occurs group-velocity dispersion that is too large to be negligible due to the objective lens or the like in the optical system in the microscope device to the observation object, a group-velocity dispersion compensation device may be provided within the short optical pulse delivery system for the purpose of compensating the group-velocity dispersion.

Seventh Embodiment

Figure 20:
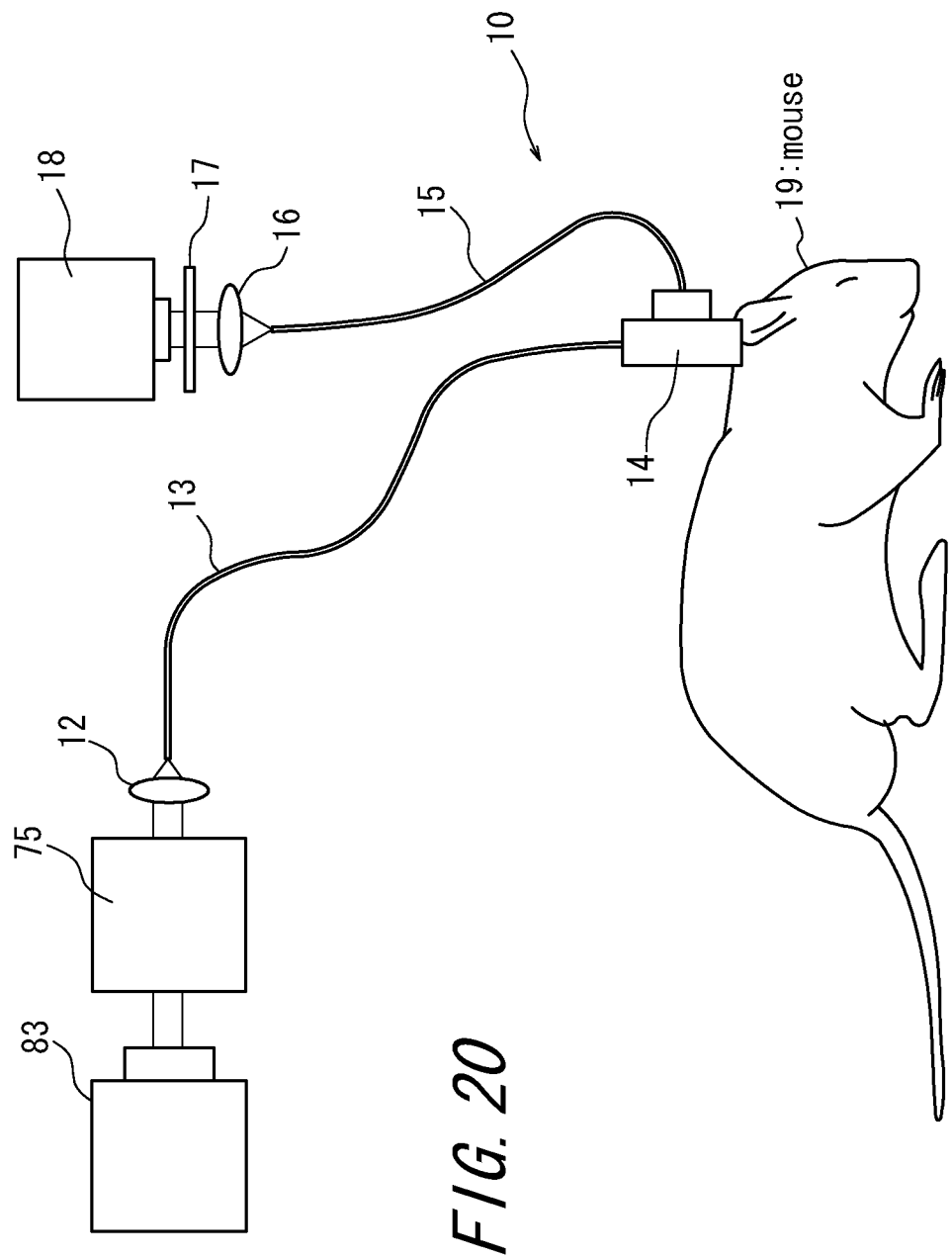
FIG. 20 is a schematic configuration diagram of a multiphoton microscope according to a seventh embodiment of the present invention.

FIG. 20 is a schematic configuration diagram of a multiphoton microscope according to a seventh embodiment of the present invention. This embodiment includes a microscope downsized as a micro head 14 arranged at a leading end of a hollow core photonic crystal fiber 13, and the micro head 14 is fixed to the head of a small laboratory animal such as a mouse, so as to observe an organ such as a mouse brain without anesthesia.

The multiphoton microscope is configured by including: a chirped light generation source 83; a chirp compensation device 75; the lens 12; the hollow core photonic crystal fiber 13; the micro head 14; the multi-mode optical fiber 15; the lens 16; the barrier filter 17; and the detector 18.

The chirped light generation source 83 is a short optical pulse source for emitting chirped pulses, and the chirp compensation device 75 disposed in the subsequent stage of the chirped light generation source 83 is a prechirper for compensating the chirp. In this embodiment, the short optical pulse source is configured by including the chirp light generation source 83 and the chirp compensation device 75.

The chirp compensation device 75 can be configured similarly to, for example, the dispersion generator 35 of FIG. 9. The short optical pulse source 83 and the chirp compensation device 75 are combined so as to form a short optical pulse source that generates unchirped short optical pulses close to the transform limit. The rest of the configuration and operation are similar to those of the first embodiment, and hence the same components are denoted by the same reference numerals and the description thereof is omitted.

As described above, according to this embodiment, a chirped light generation source for generating chirped pulses and a chirp compensation device for compensating the chirp are employed so as to form a short optical pulse source that has no chirp, and hence, when predetermined conditions are satisfied, the use of this light source produces the same effects as in the nonlinear optical device according to the fifth and sixth embodiments.

The chirp compensation device is not limited to the one that uses a pair of diffraction gratings. Various devices can be used as long as the device compensates chirp of the chirped short optical pulse source. Examples of such a device may include a device similar in configuration to the device using a prism pair that is employed as the dispersion compensation device in the fifth embodiment.

Eighth Embodiment

Figure 21:
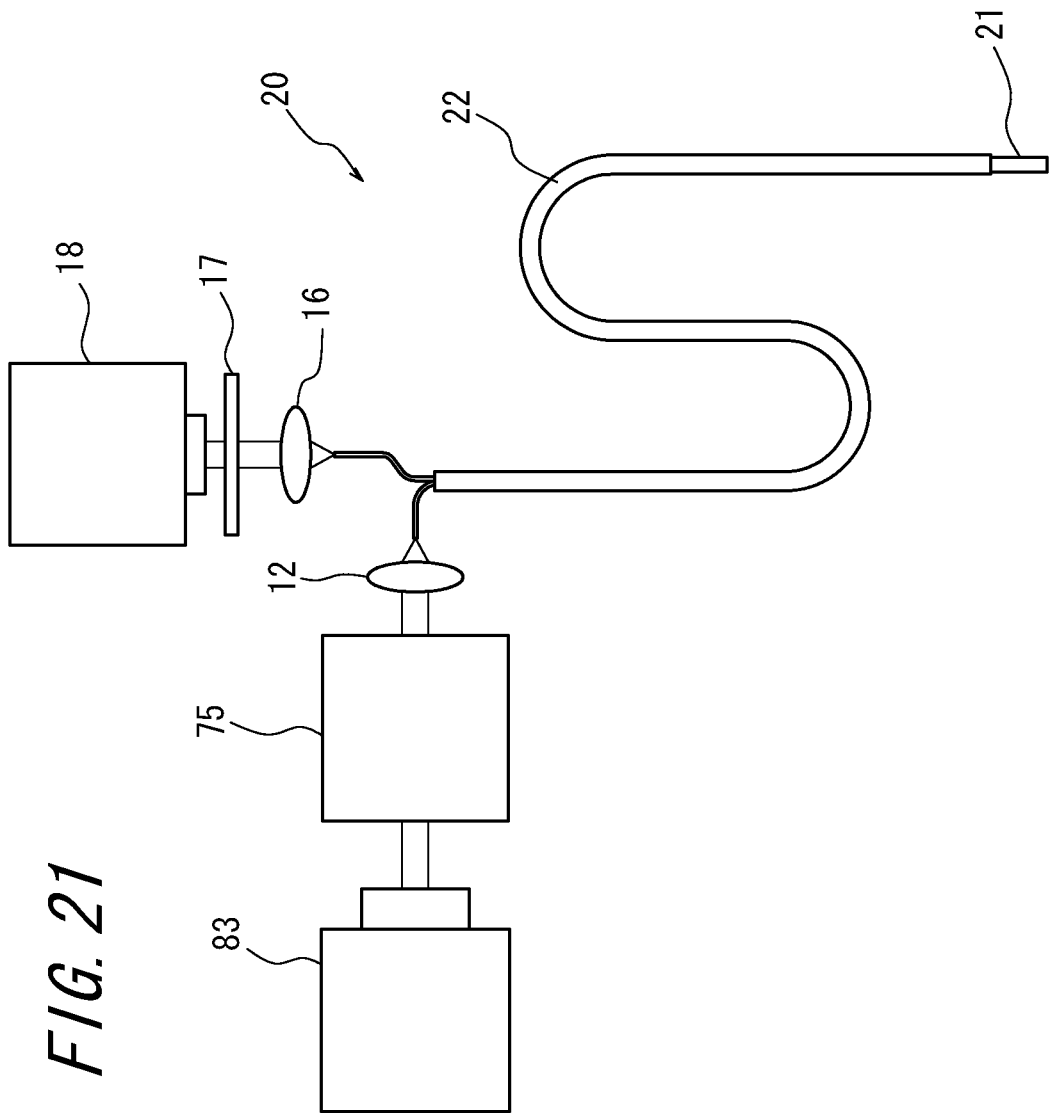
FIG. 21 is a schematic configuration diagram of an endoscope according to an eighth embodiment of the present invention.

FIG. 21 is a schematic configuration diagram of an endoscope according to an eighth embodiment of the present invention. This embodiment is different from the seventh embodiment of FIG. 20 in that the micro head 14 is formed as a hard part 21 and the hollow core photonic crystal fiber and the multi-mode fiber connected to the hard part 21 are bundled together into one so as to be configured as a flexible insertion part 22. The flexible insertion part 22 may be used alone or may be inserted into a clamp hole of a conventional endoscope, to thereby use the device as an endoscope nonlinear system 20. With this configuration, the present invention is also applicable to an endoscope and still can produce similar effects as in the seventh embodiment.

The present invention is not limited to the above-mentioned embodiments, and may be subjected to various modifications and alterations. For example, the present invention is applicable not only to the field of microscope and endoscope, but also to various fields such as material processing, as long as the application utilizes the second-order nonlinear optical effects resulting from the two-photon process. Further, the first to eighth embodiments described above each use a sech or Gaussian short optical pulse source. However, the short optical pulse source to be employed for the present invention is not limited thereto, and various other light sources can be used. In such a case, the parameter k used for calculating the spectral width (full width at half maximum) and the temporal width (full width at half maximum) of short optical pulses varies depending on the waveform of the short optical pulses. In particular, when the pulses have a waveform that is intermediate between the Gaussian waveform and the sech waveform, the value of k also falls between those of the Gaussian waveform and the sech waveform, that is, falls within a range of 0.35<k<0.55. The effect of the present invention can also be effectively obtained with respect to the short optical pulses having such a waveform.

DESCRIPTION OF SYMBOLS

1 short optical pulse source
2 short optical pulse delivery system
3 short optical pulse irradiation object
10 compact microscope nonlinear optical device
11 short optical pulse source (chirped Gaussian waveform)
12, 16, 32, 34, 52, 54 lens
13, 33, 53 hollow core photonic crystal fiber
14 micro head
14a piezo XY scanner
14b, 14d, 14f lens
14c spectral mirror
14e barrier filter
15 multi-mode fiber
17, 41, 63 barrier filter
18, 42, 64 detector
19, 39, 56 observation object
20 endoscope nonlinear optical device
21 hard part
22 insertion part
31 short optical pulse source (chirped sech waveform)
30 microscope nonlinear optical device
35 dispersion generator
35a, 35d grating
35b, 35c lens
35e, 35f mirror
36, 61 Galvano mirror pair
37 spectral mirror
38 objective lens
50 microscope nonlinear optical device
51 short optical pulse source (unchirped sech waveform)
55 objective lens
60 microscope main body
62 spectral mirror
71 group-velocity dispersion compensation device
71a, 71b prism
71c, 71d mirror
72 beam expander
72a, 72b lens
75 chirp compensation device
81 short optical pulse source (unchirped sech waveform)
82 short optical pulse source (unchirped Gaussian waveform)
83 chirped light generation source

The invention claimed is:
1. A nonlinear optical device for irradiating an object with short optical pulses so as to generate second-order nonlinear optical effects, comprising:
  a short optical pulse source for generating short optical pulses; and
  a short optical pulse delivery system for delivering, to the object, the short optical pulses generated from the short optical pulse source,
  wherein there is generated substantially no second-order nonlinear optical effect in the nonlinear optical device, there is substantially no amount of group-velocity dispersion in the nonlinear optical device, and the short optical pulses generated by the short optical pulse source have a spectral width (full width at half maximum)$\lambda_{FWHM}$ satisfying the following range:

$$\lambda_1 < \lambda_{FWHM} < \lambda_2 \tag{1}$$

under the following conditions:

$$\lambda_1 = \frac{a\lambda_c^2}{cT_2} \tag{2}$$

$$\lambda_2 = \frac{a\lambda_c^2}{cT_1} \tag{3}$$

$$T_1 = 2\sqrt{-p}\cos\left(\frac{u}{3} + \frac{4\pi}{3}\right) + \frac{(kD_{3rd})^{1/3}}{\alpha \cdot 2^{2/3}} \tag{4}$$

$$T_2 = 2\sqrt{-p}\cos\left(\frac{u}{3}\right) + \frac{(kD_{3rd})^{1/3}}{\alpha \cdot 2^{2/3}} \tag{5}$$

$$p = -\left(\frac{-1}{\alpha 2^{2/3}(kD_{3rd})^{-1/3}}\right)^2 \tag{6}$$

-continued $$u = \cos^{-1}\left(\frac{q}{p\sqrt{-p}}\right) \quad (7)$$

$$q = -\left(\frac{-1}{\alpha 2^{2/3}(kD_{3rd})^{-1/3}}\right)^3 + \frac{kD_{3rd}}{2} \quad (8)$$

where a, k: parameters determined depending on the pulse waveform, $\lambda_c$: the central wavelength of the pulses, c: the speed of light, $D_{3rd}$: the total amount of group-velocity dispersion slope, and $\alpha=0.5$.

2. The nonlinear optical device according to claim 1, wherein the following conditions are satisfied:

$$\sum_{\substack{propogation \\ medium}} \gamma \cdot P_{peak} \cdot L \leq 1 \quad (9)$$

$$\frac{D_{2d}}{T_0^2} \leq 1 \quad (10)$$

$$\frac{D_{3rd}}{T_0^3} \geq 1, \quad (11)$$

where $\gamma$ represents the nonlinear coefficient of each propagation medium in the short optical system, $P_{peak}$ represents a higher one of the peak power values of the short optical pulses before and after being delivered through each propagation medium, L represents the physical length of each propagation medium in the short optical pulse delivery system, $D_{2d}$ represents the total amount of group-velocity dispersion, $D_{3rd}$ represents the total amount of group-velocity dispersion slope, and $T_0$ represents the temporal width of the short optical pulses obtained when the output intensity of the short optical pulses becomes 1/e of the peak power in the temporal width at the Fourier transform limit calculated from the spectral width of the short optical pulses.

3. The nonlinear optical device according to claim 1, wherein the parameter k satisfies 0.35<k<0.55.

4. The nonlinear optical device according to claim 1, wherein the short optical pulse source includes: a short optical pulse generation device for generating substantially unchirped short optical pulses; and a chirp adding device for adding chirp to the short optical pulses generated from the short optical pulse generation device.

5. The nonlinear optical device according to claim 1, wherein the short optical pulse source includes a spectral width adjusting mechanism.

6. The nonlinear optical device according to claim 1, wherein the short optical pulse source generates short optical pulses having a spectral width of 0.5 nm or more.

7. The nonlinear optical device according to claim 1, wherein the short optical pulse delivery system includes a dispersion generator.

8. The nonlinear optical device according to claim 1, wherein the short optical pulse delivery system includes a hollow core photonic crystal fiber.

9. The nonlinear optical device according to claim 8, wherein the short optical pulse source emits short optical pulses having a wavelength at which the hollow core photonic crystal fiber has group-velocity dispersion reduced to zero.

10. The nonlinear optical device according to claim 8, wherein the short optical pulse source emits short optical pulses having a wavelength at which the nonlinear optical device has total group-velocity dispersion reduced to zero.

11. A multiphoton microscope comprising the nonlinear optical device according to claim 1, wherein second-order nonlinear effects generated from the object are detected.

12. An endoscope comprising the nonlinear optical device according to claim 1, wherein second-order nonlinear effects generated from the object are detected.

13. A nonlinear optical device for irradiating an object with short optical pulses so as to generate second-order nonlinear optical effects, comprising:

a short optical pulse source for generating short optical pulses; and a short optical pulse delivery system for delivering the short optical pulses generated from the short optical pulse source to the object, wherein there is generated substantially no second-order nonlinear optical effect in the nonlinear optical device, there is substantially no amount of group-velocity dispersion in the nonlinear optical device, and the short optical pulses generated by the short optical pulse source have a pulse temporal width (full width at half maximum) $T_{FWHM}$ satisfying the following range:

$$T_1 < T_{FWHM} < T_2 \quad (13)$$

under the following conditions:

$$T_1 = 2\sqrt{-p}\cos\left(\frac{u}{3} + \frac{4\pi}{3}\right) + \frac{(kD_{3rd})^{1/3}}{\alpha \cdot 2^{2/3}} \quad (14)$$

$$T_2 = 2\sqrt{-p}\cos\left(\frac{u}{3}\right) + \frac{(kD_{3rd})^{1/3}}{\alpha \cdot 2^{2/3}} \quad (15)$$

$$p = -\left(\frac{-1}{\alpha 2^{2/3}(kD_{3rd})^{-1/3}}\right)^2 \quad (16)$$

$$u = \cos^{-1}\left(\frac{q}{p\sqrt{-p}}\right) \quad (17)$$

$$q = -\left(\frac{-1}{\alpha 2^{2/3}(kD_{3rd})^{-1/3}}\right)^3 + \frac{kD_{3rd}}{2} \quad (18)$$

where k: parameter determined depending on the pulse waveform, $D_{3rd}$: the total amount of group-velocity dispersion slope, and $\alpha=0.5$.

14. The nonlinear optical device according to claim 13, wherein the following conditions are satisfied:

$$\sum_{\substack{propogation \\ medium}} \gamma \cdot P_{peak} \cdot L \leq 1 \quad (19)$$

$$\frac{D_{2d}}{T_0^2} \leq 1 \quad (20)$$

$$\frac{D_{3rd}}{T_0^3} \geq 1 \quad (21)$$

where $\gamma$ represents the nonlinear coefficient of each propagation medium in the short optical system, $P_{peak}$ represents a higher one of the peak power values of the short optical pulses before and after being delivered through each propagation medium, L represents the physical length of each propagation medium in the short optical pulse delivery system, $D_{2d}$ represents the total amount of group-velocity dispersion, $D_{3rd}$ represents the total amount of group-velocity dispersion slope, and $T_0$ represents the temporal width of the short optical pulses obtained when the output intensity of the short optical pulses becomes 1/e of the peak power.

15. The nonlinear optical device according to claim 13, wherein the short optical pulse source generates short optical pulses satisfying the following expression:

$$T_{FWHM} f_{FWHM} \leq 0.88 \quad (22)$$

where $f_{FWHM}$ represents the spectral half width (full width at half maximum) of the short optical pulses generated by the short optical pulse source.

16. The nonlinear optical device according to claim 13, wherein the parameter k satisfies 0.35<k<0.55.

17. The nonlinear optical device according to claim 13, wherein the short optical pulse source includes: a short optical pulse generation device for generating chirped short optical pulses; and a chirp compensation device for compensating chirp of the short optical pulses generated from the short optical pulse generation device.

18. The nonlinear optical device according to claim 17, wherein the chirp compensation device includes a diffraction grating.

19. The nonlinear optical device according to claim 17, wherein the chirp compensation device includes a prism.

20. The nonlinear optical device according to claim 13, wherein the short optical pulse delivery system includes a group-velocity dispersion compensation device.

21. The nonlinear optical device according to claim 20, wherein the group-velocity dispersion compensation device includes a diffraction grating.

22. The nonlinear optical device according to claim 20 wherein the group-velocity dispersion compensation device includes a prism.

23. The nonlinear optical device according to claim 13, wherein the short optical pulse delivery system includes a hollow core photonic crystal fiber.

24. The nonlinear optical device according to claim 13, wherein the short optical pulse source generates short optical pulses having a temporal width of 1 picosecond or less.

25. A multiphoton microscope comprising the nonlinear optical device according to claim 13, wherein second-order nonlinear effects generated by the object are detected.

26. An endoscope comprising the nonlinear optical device according to claim 13, wherein second-order nonlinear effects generated by the object are detected.

* * * * *